(12) United States Patent
Yamazaki et al.

(10) Patent No.: US 11,172,887 B2
(45) Date of Patent: Nov. 16, 2021

(54) VEHICULAR AIRBAG DEVICE

(71) Applicant: Autoliv Development AB, Vårgårda (SE)

(72) Inventors: Yuki Yamazaki, Yokohama (JP); Tatsuya Harada, Yokohama (JP); Yukinori Midorikawa, Yokohama (JP)

(73) Assignee: AUTOLIV DEVELOPMENT AB, Vargarda (SE)

( * ) Notice: Subject to any disclaimer, the term of this patent is extended or adjusted under 35 U.S.C. 154(b) by 249 days.

(21) Appl. No.: 15/301,253

(22) PCT Filed: Feb. 12, 2015

(86) PCT No.: PCT/JP2015/053741
§ 371 (c)(1),
(2) Date: Sep. 30, 2016

(87) PCT Pub. No.: WO2015/151595
PCT Pub. Date: Oct. 8, 2015

(65) Prior Publication Data
US 2017/0014078 A1    Jan. 19, 2017

(30) Foreign Application Priority Data
Apr. 4, 2014 (JP) .............................. JP2014-077503

(51) Int. Cl.
*A61B 5/00* (2006.01)
*A61B 5/0245* (2006.01)
(Continued)

(52) U.S. Cl.
CPC .......... *A61B 5/6893* (2013.01); *A61B 5/0245* (2013.01); *A61B 5/7225* (2013.01);
(Continued)

(58) Field of Classification Search
CPC ... A61B 5/0245; A61B 5/6893; A61B 5/7225; B62D 1/046; B62D 1/065; H05B 1/0236; H05B 3/03
(Continued)

(56) References Cited

U.S. PATENT DOCUMENTS 3,801,800 A * 4/1974 Newton ............. A61B 18/1206
327/514
3,880,146 A * 4/1975 Everett ................ A61B 5/0006
600/523
(Continued)

FOREIGN PATENT DOCUMENTS

| JP | 9-76922 | 3/1997 |
|---|---|---|
| JP | 11-347007 | 12/1999 |

(Continued)

OTHER PUBLICATIONS

English Translation of JP2000-23929A.*
PCT International Search Report—dated Apr. 7, 2015.

*Primary Examiner* — Erin E McGrath
(74) *Attorney, Agent, or Firm* — Dickinson Wright PLLC

(57) ABSTRACT

An occupant information sensing device 100 includes a plurality of heater electrodes that are provided at a vehicle steering wheel 104 and insulated and separated from one another and that generate heat by conduction. Power sources provide electrical current for heater electrodes. Electrical circuit elements enable the system to provide occupant biological condition monitoring, gripping detection, and electrical stimulation. The circuits enable common electrical connecting to the heater electrodes to provide multiple functions through the use of filtering and time division multiplexing.

9 Claims, 15 Drawing Sheets

(51) Int. Cl.
*B62D 1/04* (2006.01)
*B62D 1/06* (2006.01)
*H05B 3/03* (2006.01)
*H05B 1/02* (2006.01)

(52) U.S. Cl.
CPC ............. *B62D 1/046* (2013.01); *B62D 1/065* (2013.01); *H05B 1/0236* (2013.01); *H05B 3/03* (2013.01); *H05B 2203/037* (2013.01)

(58) Field of Classification Search
USPC ......................................................... 219/204
See application file for complete search history.

(56) References Cited

U.S. PATENT DOCUMENTS

| 4,517,982 | A | * | 5/1985 | Shiga | A61B 5/0245 |
| | | | | | 600/358 |
| 4,572,207 | A | * | 2/1986 | Yoshimi | A61B 5/0245 |
| | | | | | 600/382 |
| 4,722,343 | A | * | 2/1988 | Lombardi | A61N 1/36014 |
| | | | | | 600/554 |
| 4,909,261 | A | * | 3/1990 | Rothenberg | A61B 5/04886 |
| | | | | | 600/547 |
| 4,924,397 | A | * | 5/1990 | Kurihara | B60K 31/047 |
| | | | | | 180/179 |
| 6,430,436 | B1 | * | 8/2002 | Richter | A61B 5/0245 |
| | | | | | 600/520 |
| 6,590,493 | B1 | * | 7/2003 | Rasimas | H04B 3/56 |
| | | | | | 340/538.12 |
| 2006/0284839 | A1 | * | 12/2006 | Breed | B60W 50/16 |
| | | | | | 345/156 |
| 2008/0143504 | A1 | * | 6/2008 | Martin Alvarez | B60K 28/066 |
| | | | | | 340/439 |
| 2013/0092677 | A1 | * | 4/2013 | Virnich | B60N 2/5685 |
| | | | | | 219/204 |
| 2013/0150743 | A1 | * | 6/2013 | Tomimori | A61B 5/6893 |
| | | | | | 600/521 |
| 2014/0151356 | A1 | * | 6/2014 | Maguire | B62D 1/046 |
| | | | | | 219/204 |
| 2015/0102024 | A1 | * | 4/2015 | Barfuss | B62D 1/046 |
| | | | | | 219/204 |

FOREIGN PATENT DOCUMENTS

| JP | 2000-23929 | | 1/2000 | | |
| JP | 2000-23929 | A * | 1/2000 | ........... | A61B 5/0245 |
| JP | 2011-156215 | | 8/2001 | | |
| JP | 3451615 | | 7/2003 | | |
| JP | 2008-225476 | | 9/2008 | | |

* cited by examiner (a)

(b)

(a)

(b)

(a)

(b)

VEHICULAR AIRBAG DEVICE

CROSS REFERENCE TO RELATED APPLICATIONS

This application claims priority to Japanese Patent Application No. 2014-077503, filed on Apr. 4, 2014 and PCT/JP2015/053741, filed on Feb. 12, 2015.

FIELD OF THE INVENTION

The present invention relates to an occupant information sensing device provided at a vehicle steering wheel and including a plurality of heater electrodes.

BACKGROUND

In recent years, various types of vehicle steering including an additional function, such as a heater function for keeping an occupant warm, which is provided in addition to the function of an operation means gripped by the occupant, have been developed. For example, Japanese Patent Application Publication No. H09-76922 discloses a heater-attached steering wheel additionally provided with a heater function by a heat generator that covers the steering wheel. According to Japanese Patent Application Publication No. H09-76922, the heat generator connected with a battery is controlled by switching operation so that it is provided with power and then the conduction is stopped after a prescribed time period, which prevents the steering wheel from being heated more than necessary.

Japanese Patent Application Publication No. 2011-156215 discloses a steering wheel provided with an electrode for biological signal to obtain a biological signal from an occupant driving the vehicle. According to Japanese Patent Application Publication No. 2011-156215, biological information such as an ECG waveform is measured by an operation circuit on the basis of the obtained biological signal.

Japanese Patent Application Publication No. 2008-59459 discloses a device provided with a gripping detecting means for detecting whether an occupant has gripped a steering wheel and adapted to issue warning depending on the gripping state of steering.

The above cited prior art references disclose an arrangement including, as an additional function, one of the heater function for a steering wheel, the function of measuring biological information, and the function of detecting a steering wheel gripping state. PTL 4 further discloses a heater-attached steering wheel including a heartbeat detecting function for detecting the heartbeat of an occupant driving the vehicle.

According to Japanese Patent Application Publication No. 2000-23929, the heater-attached steering wheel is provided with an electrode for heartbeat detection and a heater electrode as a heat generator separately in order to implement the heater function and the heartbeat detecting function. More specifically, the heater electrode is conducted for heat generation, and the heartbeat of the occupant is also detected through the electrode for heartbeat detection when the occupant grips the steering wheel. Herein, a signal indicating occupant's biological information (such as a heartbeat) and a signal indicating a steering wheel gripping state by the occupant are generically referred to as examples of an occupant information signal.

Japanese Patent Application Publication No. 2000-23929 merely discloses an arrangement in which an occupant information signal is output from another electrode different from the heater electrode. More specifically, according to the techniques disclosed by the above-mentioned references, the steering wheel must be provided with an additional electrode in addition to the heater electrode in order to add another function to the heater function, which could complicate the structure and increase the manufacturing cost.

The present invention is directed to a solution to the problem and it is an object of the present invention to provide an occupant information sensing device capable of processing an occupant information signal using a heater electrode.

SUMMARY AND INTRODUCTORY DESCRIPTION OF THE INVENTION

In order to solve the above-described problem, a typical arrangement of an occupant information sensing device according to the present invention includes: a plurality of heater electrodes that are provided at a vehicle steering wheel and insulated and separated from one another and that generate heat by conduction; at least one first heater power source of an insulated type DC power source that feeds power to at least two heater electrodes of the plurality of heater electrodes; and a signal processing circuit that is connected to the heater electrode through a capacitor and processes an occupant information signal output from the heater electrode.

In the above-described arrangement, the first heater power source of the insulated type DC power source supplies at least two arbitrary heater electrodes of the plurality of electrodes with heater power. The heater electrode is supplied with the heater power to generate heat and serves as a heater. The heater electrode can output an occupant information signal such as a heartbeat regardless of whether the heater electrode is supplied with the heater power. The heater electrode connected with the signal processing circuit through the capacitor includes an electrode that is not supplied with the heater power (i.e. not connected to an electrical potential source for generating resistive heating).

The occupant information signal is for example a signal indicative of biological information of the occupant (such as a heartbeat) and gripping information about the steering wheel by the occupant (gripping state), and these occupant information signals are indicated as AC components. In the above-described arrangement, the heater electrode and a circuit that processes the occupant information signals (signal processing circuit) are connected through a DC cut (filter) capacitor. The occupant information signal output from the heater electrode has its DC component filtered out by the capacitor. The AC component of the occupant information signal indicating occupant information is received by the signal processing circuit. The signal processing circuit is a circuit that carries out appropriate processing such as detection of a heartbeat of the occupant and a gripping state of the steering wheel on the basis of the received occupant information signals. In the above-described arrangement, the occupant information signals can be processed using the heater electrodes. In the above-described arrangement, various functions in addition to the heater function can be implemented without using another electrode different from the heater electrodes. The first heater power source of the insulated type DC power source is apparently grounded through the occupant (human body) from the heater electrode.

The above-described filter capacitor may be connected to the input of the signal processing circuit. In this way, the signal processing circuit attains a floating state with respect to the DC component of a signal by the DC cut capacitor. The DC component of the occupant information signal output from the heater electrode can be cut and an unwanted signal component can be reduced.

The occupant information sensing device may further include a switching element that is provided part-way in a circuit from the first power source to the heater electrode and establishes a conduction state or a non-conduction state between the first heater power source and the heater electrode. The heater function can be activated or deactivated by controlling the switching element.

The occupant information sensing device may further include a control circuit that switches the switching element by time division, and the control circuit may connect the heater electrode to one of the first heater power source and the signal processing circuit at prescribed time intervals. When the control circuit connects the heater electrode and the first heater power source by controlling the switching element, the heater function can be activated. When the control circuit connects the heater electrode and the signal processing circuit by controlling the switching element, the processing by the signal processing can be activated. In the above-described arrangement, the switching element is switched by time-division multiplexing, so that the signal processing circuit as well as the heater function can be independently controlled.

The above-described signal processing circuit may include a heartbeat detecting circuit that detects the heartbeat of the occupant by differentially amplifying the heartbeat signals from the occupant output from the at least two heater electrodes. In this way, the heartbeat detecting function as well as the heater function can be implemented using the heater electrodes.

The above-described signal processing circuit may further include a first signal generating circuit that inputs a first signal to one of the at least two heater electrodes and a gripping detecting circuit that detects a state of gripping the steering wheel by the occupant on the basis of a second signal, with the first signal, which has passed through the occupant in contact with one and the other of the at least two heater electrodes, being output from the other as the second signal. In this way, the gripping detecting function as well as the heater function can be implemented using the heater electrodes. Note that the gripping detecting function may be arranged in addition to the above-described heartbeat detecting function. Alternatively, the gripping detecting function may be arranged alone.

Another typical arrangement of the occupant information sensing device according to the present invention includes: a plurality of heater electrodes that are provided at a vehicle steering wheel and insulated and separated from one another and that generate heat by conduction; a second heater power source of a non-insulated type AC power source that feeds power to at least two heater electrodes of the plurality of heater electrodes and that is grounded commonly for the heater electrodes; a filter that is provided part-way in a circuit from the second heater power source to the heater electrode to pass a frequency of the AC power source of the second heater power source and blocks a frequency of an occupant information signal output from the heater electrode; and a signal processing circuit that processes the occupant information signal, wherein the AC power source of the second heater power source uses a frequency different from the occupant information signal, and an input portion of the signal processing circuit is connected between the filter and the heater electrode.

In the above-described arrangement, the filter is provided part-way in the circuit from the second heater power source to the heater electrode, and the input portion of the signal processing circuit is connected between the filter and the heater electrode. The occupant information signal output from the heater electrode is blocked by the filter, is not passed to the non-insulated type, second heater power source that can be regarded as having low input impedance and is received at the signal processing circuit. On the other hand, a different frequency from the occupant information signal is used as the frequency of the AC power source of the second heater power source, so that the second heater power source can supply the heater electrodes with heater power passing through the filter and the heater function can be implemented. In the above-described arrangement, the occupant information signal can be processed using the heater electrodes. In the above-described arrangement, various functions by the signal processing circuit as well as the heater function can be implemented without using another electrode different from the heater electrodes.

The occupant information sensing device may further include a switching element that is provided part-way in a circuit from the second heater power source to the heater electrode, and the switching element may establish a conduction state or a non-conduction state between the second heater power source and the heater electrode. The heater function can be activated or deactivated by controlling the switching element.

The occupant information sensing device may further include a control circuit that switches the switching element by time division multiplexing, and the control circuit may connect the heater electrode to one of the second heater power source and the signal processing circuit at prescribed time intervals. The control circuit can control the signal processing circuit as well as the heater function by controlling the switching element by time division multiplexing.

The occupant information signal is a heartbeat signal from an occupant in one example, and the signal processing circuit may include a heartbeat detecting circuit that detects heartbeat signals from the occupant output from the at least two heater electrodes, and the filter may be a high-pass filter that blocks a frequency of the heartbeat signal. The heartbeat signal is blocked by the high-pass filter and is not passed to the side of the second heater power source but is surely received at the heartbeat detecting circuit. Therefore, using the heater electrodes, the heartbeat detecting function as well as the heater function can be implemented.

The occupant information signal may be a gripping state detection signal indicative of a state of gripping the steering wheel by the occupant, the signal processing circuit may further include a first signal generating circuit that inputs a first signal to one of the at least two heater electrodes and a gripping detecting circuit that detects the state of gripping the steering wheel by the occupant on the basis of a second signal included in the gripping state detection signal, with the first signal, which has passed through the occupant in contact with one and the other of the at least two heater electrodes, being output from the other as the gripping state detection signal, and the filter may be a low-pass filter that blocks a frequency of the gipping state detection signal. In this way, the gripping state detection signal is blocked by the low-pass filter, not passed to the side of the second heater power source and can surely be received at the gripping detecting circuit. Therefore, the heartbeat detecting function as well as the heater function can be implemented using the heater electrodes.

The occupant information signal may be a heartbeat signal from the occupant and also may be a gripping state detection signal indicative of a state of gripping the steering wheel by the occupant, the signal processing circuit may include a heartbeat detecting circuit that detects heartbeat signals from the occupant output from the at least two heater electrodes, a first signal generating circuit that inputs a first signal to one of the at least two heater electrodes, and a gripping detecting circuit that detects the state of gripping the steering wheel by the occupant on the basis of a second signal included in the gripping state detection signal, with the first signal, which has passed through the occupant in contact with one and the other of the at least two heater electrodes, being output from the other as the gripping state detection signal, and the filter may be a band-pass filter that blocks a frequency of the heartbeat signal and a frequency of the gripping state detection signal. In this way, the heartbeat signal and the gripping state detection signal are blocked by the band-pass filter and not passed to the side of the second heater power source but can surely be received at the heartbeat detecting circuit and the gripping detecting circuit, respectively. Therefore, the heartbeat detecting function as well as the heater function can be implemented using the heater electrodes.

Another typical arrangement of an occupant information sensing device according to the present invention includes: a plurality of heater electrodes that are provided at a vehicle steering wheel and insulated and separated from one another and that generate heat by conduction; a second heater power source of a non-insulated type AC power source that feeds power to at least two heater electrodes of the plurality of heater electrodes and that is grounded commonly for the heater electrodes; a signal processing circuit that processes an occupant information signal output from the heater electrode; a switching element that is provided part-way in a circuit from the second heater power source to the heater electrode and establishes a conduction state or a non-conduction state between the second heater power source and the heater electrode; a control circuit that switches the switching element by time division multiplexing and connects the heater electrode to one of the second heater power source and the signal processing circuit at prescribed time interval.

In the above-described arrangement, when the control circuit connects the heater electrode and the second heater power source by controlling the switching element, the heater function can be activated. On the other hand, when the heater electrode and the signal processing circuit are connected, the occupant information signal is not passed to the side of the non-insulated type, second heater power source that can be regarded as having low impedance and is received at the signal processing circuit. Therefore, the processing by the signal processing circuit can be activated. Therefore, in the above-described arrangement, various functions by the signal processing circuit as well as the heater function can be implemented using the heater electrodes by switching the switching element by time division.

According to the present invention, an occupant information sensing device capable of processing an occupant information signal using a heater electrode can be provided.

DETAILED DESCRIPTION OF THE INVENTION

Figure 1:
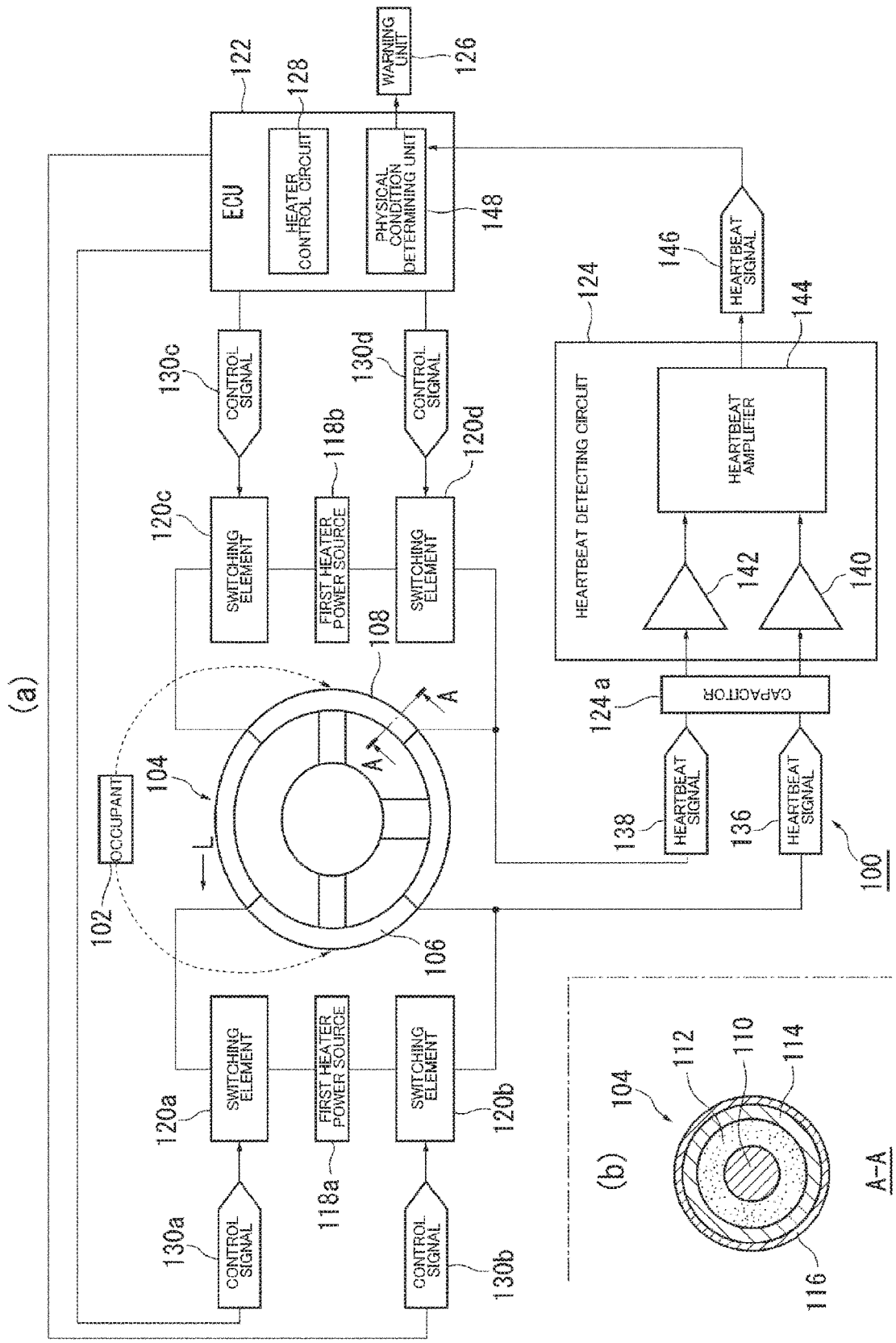
FIG. 1(a) is an exemplary diagram of an occupant information sensing device according to a first embodiment of the present invention.
FIG. 1(b) is a cross-sectional view taken along line A-A in FIG. 1(a)

Now, preferred embodiments of the present invention will be described in detail with reference to the accompanying drawings. The sizes, materials, other specific numerical values, etc., in the following description of the embodiment are simply examples for the ease of understanding of the invention and should not be construed to limit the invention unless otherwise specified. Note that in the description and the drawings, elements having substantially identical functions and structures are designated by the same reference characters, and a repeated description of them will be omitted, while elements that are not directly relevant to the present invention are not shown.

FIG. 1 is an exemplary diagram of an occupant information sensing device 100 according to a first embodiment of the present invention. FIG. 1(a) is a functional block diagram of the occupant information sensing device 100. FIG. 1(b) is a sectional view taken along line A-A in FIG. 1(a).

The occupant information sensing device 100 includes a steering wheel 104 gripped by both hands of an occupant 102 in a vehicle. The steering wheel 104 has an electrode for left hand (heater electrode 106) provided on the left side in the vehicle-widthwise direction as indicated by the arrow L in FIG. 1(a) and an electrode for right hand (heater electrode 108) provided on the right side in the vehicle-widthwise direction. These heater electrodes 106 and 108 are conductors positioned on the surface of the steering wheel 104, insulated and separated from each other, and through which electrical current is passed to generate heat.

As illustrated in FIG. 1(b), the steering wheel 104 is for example a leather trimmed type steering wheel having a core 110 for example of aluminum or magnesium, a urethane layer 112 covering the core 110, a piece of leather 114 wrapped around the urethane layer 112, and a conductor layer 116 (the heater electrode 108 in this example) positioned immediately on the piece of leather 114. The conductor layer 116 may be formed by wrapping the leather piece 114 with a sheet-like heating body (resistor) or applying a conductive paint containing carbon or metal powder directly on the leather piece. If the steering wheel 104 is not a leathered type steering wheel, the conductor layer 116 may be formed directly on the urethane layer 112.

The occupant information sensing device 100 includes first heater power sources 118a and 118b of insulated type DC power sources, switching elements 120a to 120d, an ECU 122, a signal processing circuit (heartbeat detecting circuit 124), a capacitor 124a, and a warning unit 126. The first heater power sources 118a and 118b supply (feed) the heater electrodes 106 and 108 with heater power, respectively. The heater electrodes 106 and 108 are fed by the first heater power sources 118a and 118b to generate heat and serve as heaters.

The switching elements 120a to 120d are positioned part-way in a circuit from the first heater power sources 118a and 118b to the heater electrodes 106 and 108 and are provided in series on the input side and the output side of the heater electrodes 106 and 108, respectively. The switching elements 120a to 120d are for example FETs (field effect transistors). The switching elements 120a to 120d establish a conduction state or a non-conduction state between the first heater power sources 118a and 118b and the heater electrodes 106 and 108 in response to control signals 130a to 130d from a heater control circuit 128 in the ECU 122. More specifically, the heater control circuit 128 can set whether or not to cause the heater electrodes 106 and 108 to generate heat and activate or deactivate the heater function by controlling the switching elements 120a to 120d.

Here, when the left hand of the occupant 102 contacts the heater electrode 106 and the right hand contacts the heater electrode 108, the occupant 102 is interposed as a dielectric between the heater electrodes 106 and 108 forming an electrode pair and an electrical circuit. In this state, heartbeat signals 136 and 138 as occupant information signals are output from the heater electrodes 106 and 108 through the occupant 102 as a dielectric.

The heartbeat signals 136 and 138 are signals indicating heartbeats an example of biological information about the occupant 102, and the heartbeats are indicated as AC components. As shown in FIG. 1(a), the heartbeat detecting circuit 124 is connected with the heater electrodes 106 and 108 through a DC cut capacitor 124a. The DC components of the heartbeat signals 136 and 138 output from the heater electrodes 106 and 108 are cut (not passed through capacitor 124a) by the capacitor 124a. The AC components of the heartbeat signals 136 and 138 indicating the heartbeats passed through capacitor 124a and are received by the heartbeat detecting circuit 124. The first heater power sources 118a and 118b are apparently earthed (grounded) through the occupant 102 from the heater electrodes 106 and 108.

The heartbeat signals 136 and 138 have their DC components cut by the capacitor 124a and their AC components indicating the heartbeats are input to a heartbeat amplifier 144 through analog circuits 140 and 142 as an input portion (signal receiver) of the heartbeat detecting circuit 124. More specifically, the capacitor 124a is connected to the input portion of the heartbeat detecting circuit 124. The heartbeat signals 136 and 138 are weak signals (several mV). Therefore, the heartbeat amplifier 144 converts the AC components of the input heartbeat signals 136 and 138 into a readable level at the ECU 122 by carrying out differential amplification and filtering and produces a heartbeat signal 146.

The heartbeat signal 146 is output from the heartbeat detecting circuit 124 and then input to a physical condition determining unit 148 in the ECU 122. The physical condition determining unit 148 determines the physical condition of the occupant 102 on the basis of the heartbeat signal 146. The physical condition determining unit 148 determines, for instance, whether the occupant 102 is dozing off or caught by a health abnormality such as ventricular fibrillation using the heartbeat signal 146 as so-called heartbeat information.

The warning unit 126 makes prescribed warning if an abnormality is detected by the physical condition determining unit 148. For example, the warning unit 126 can output warning using a speaker in the vehicle or the navigation screen of a car navigator to warn the occupant 102 of the abnormality.

Figure 2:
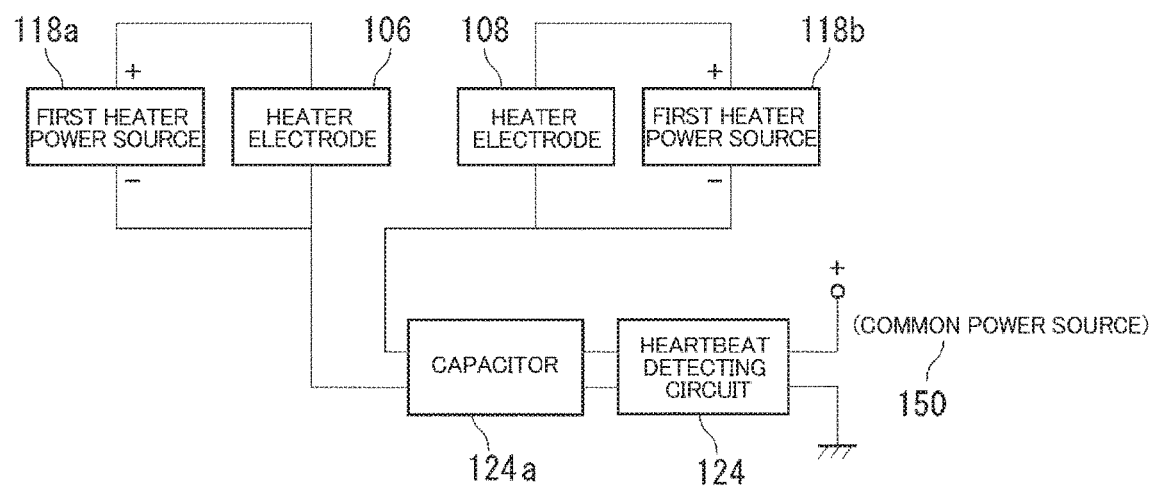
FIGS. 2(a) and 2(b) are a diagrams for illustrating a first heater power source in the occupant information sensing device in FIG. 1.
Figure 2:
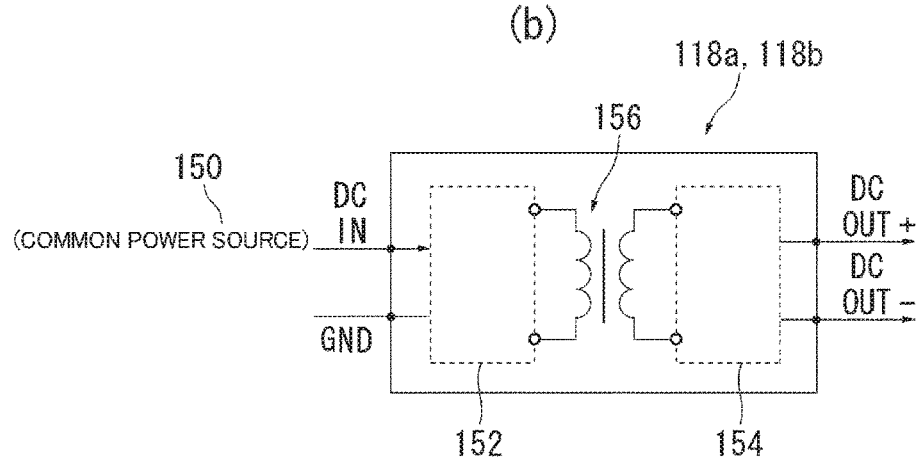

FIGS. 2(a) and (b) are diagrams for illustrating the first heater power sources 118a and 118b in the occupant information sensing device 100 shown in FIG. 1. FIG. 2(a) is an exemplary functional block diagram showing a part of the occupant information sensing device 100 in FIG. 1(a). FIG. 2(b) is an exemplary schematic diagram of a circuit configuration of the first heater power sources 118a and 118b in FIG. 1(b).

The first heater power sources 118a and 118b are insulated type DC power sources and attain an electrically floating (insulated) state with respect to a common power source 150 for the entire circuit including the heartbeat detecting circuit 124 as illustrated in FIG. 2(a). More specifically, as illustrated in FIG. 2(b), in the first heater power sources 118a and 118b, a transformer 156 is interposed between an input side circuit 152 connected to the common power source 150 to receive applied voltage and an output side circuit 154 that outputs prescribed voltage. First heater power sources 118a and 118b have internal electronic components enabling the DC input to be internally converted to an AC voltage which can be stepped up or reduced through transformer 156 with a rectifier on the DC output side. Alternatively, other types of electronic elements for stepping up or reducing DC power levels can be employed within first heater power sources 118a and 118b. Therefore, in the first heater power sources 118a and 118b, the input side circuit 152 and the output side circuit 154 are insulated from each other and are thus insulated from the heartbeat detecting circuit 124 DC power-wise as a result. The first heater power sources 118a and 118b are insulated type power sources but can supply the heater electrodes 106 and 108 with heater power, so that the output impedance is basically low input impedance.

The occupant information sensing device 100 cuts the DC components of weak heartbeat signals 136 and 138 output from the heater electrodes 106 and 108 using the capacitor 124a and can receive the heartbeat signal 146 as an AC component indicating the heartbeat at the heartbeat detecting circuit 124.

Figure 3:
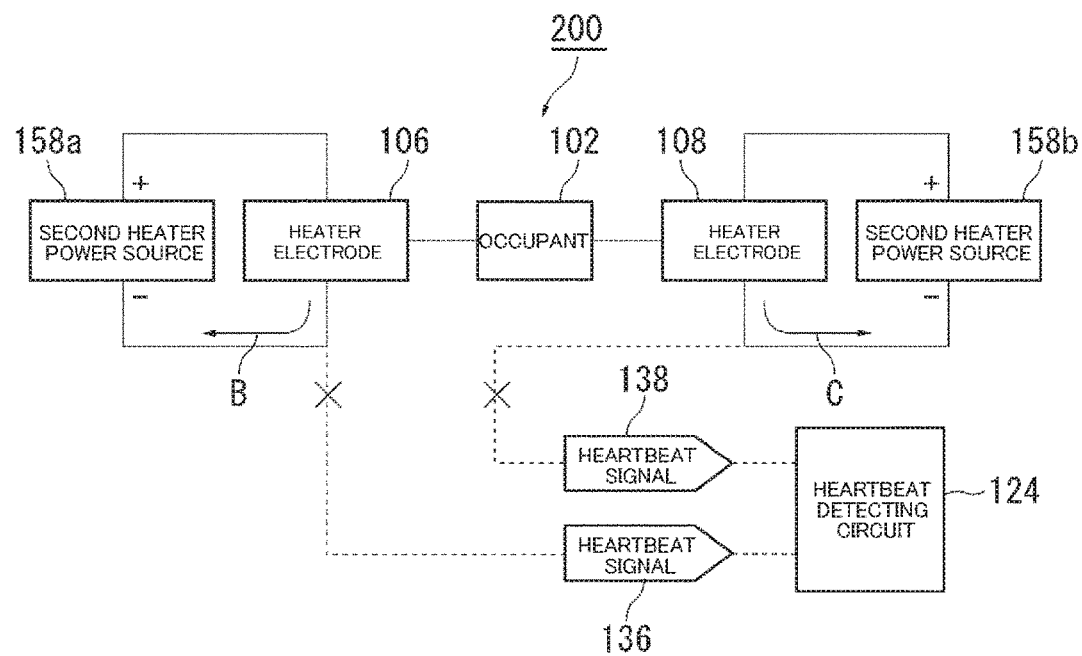
FIG. 3 is an exemplary schematic diagram of an occupant information sensing device according to a comparative example.

FIG. 3 is an exemplary schematic diagram of an occupant information sensing device 200 according to a comparative example. The occupant information sensing device 200 includes non-insulated type AC power sources, second heater power sources 158a and 158b in place of the first heater power sources 118a and 118b as the insulated type DC power sources. The second heater power sources 158a and 158b for example do not include the transformer 156 illustrated in FIG. 2(b) and are not insulated from the common power source 150 (see FIG. 2(a)). Note that the common power source 150 may serve as the second heater power sources 158a and 158b.

Here, the contact resistance between the surface of the skin of the occupant 102 (human body) and the heater electrodes 106 and 108 as conductors is at least several kΩ. Therefore, the heartbeat detecting circuit 124 needs high input impedance (for example about from 400 kΩ to 10 TΩ) in order to detect the weak heartbeat signals 136 and 138. In the context, the non-insulated, second heater power sources 158a and 158b may be regarded as having low input impedance with respect to a human body. As a result, the heartbeat signals 136 and 138 are passed to the side of the second heater power sources 158a and 158b and cannot be detected by the heartbeat detecting circuit 124 as indicated by the arrows B and C in FIG. 3.

In contrast, in the occupant information sensing device 100 according to the first embodiment, the insulated-type, first heater power sources 118a and 118b are used, and the heater electrodes 106 and 108 and the heartbeat detecting circuit 124 are connected through the capacitor 124a. In this way, the heartbeat signal 146 indicative of the AC components of the heartbeat signals 136 and 138 can be received at the heartbeat detecting circuit 124. Therefore, in the occupant information sensing device 100, using the same devices, i.e., the heater electrodes 106 and 108, the heater function as well as the heartbeat detecting function can be implemented. The two first heater power sources 118a and 118b are provided to feed power to the heater electrodes 106 and 108, respectively, while alternatively a single common first heater power source may be provided.

Figure 4:
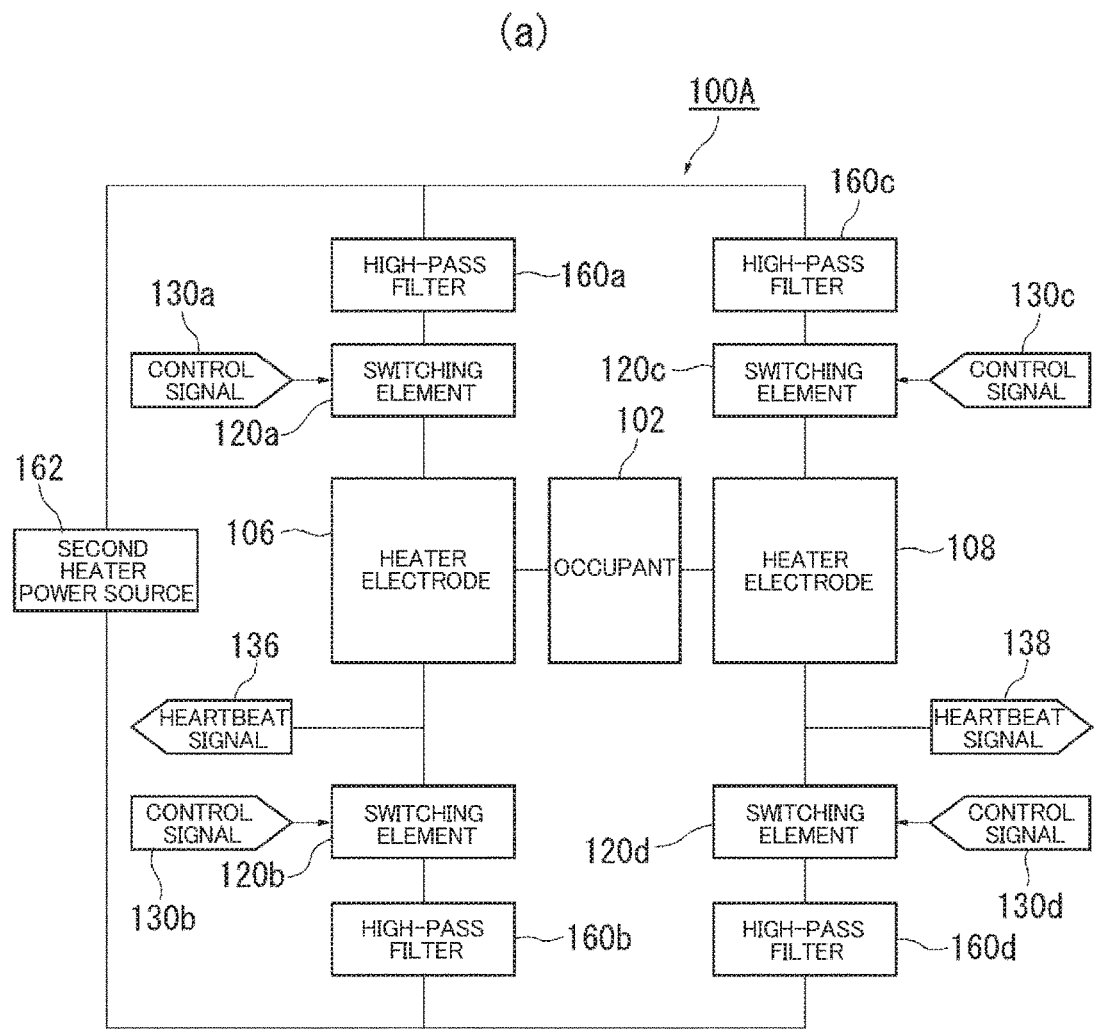
FIGS. 4(a) and 4(b) are exemplary schematic diagrams of an occupant information sensing device according to a second embodiment of the present invention.
Figure 4:
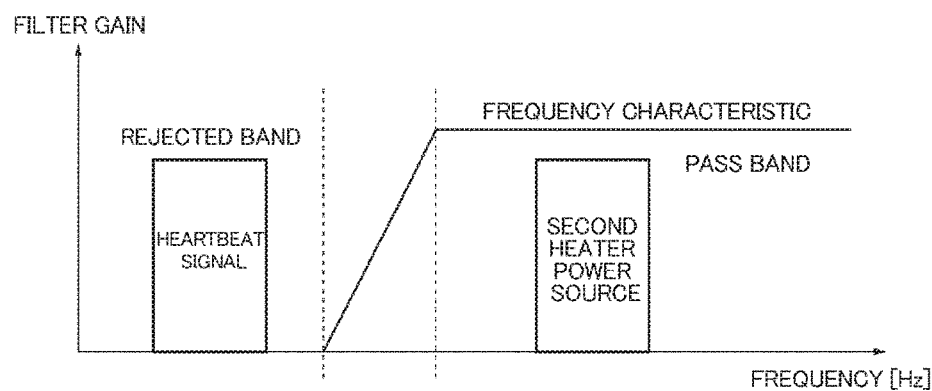

FIGS. 4(a) and (b) are exemplary schematic diagrams of an occupant information sensing device 100A according to a second embodiment of the present invention. FIG. 4(a) is an exemplary functional block diagram showing a part of the occupant information sensing device 100A. In the figure, the ECU 122, the heartbeat detecting circuit 124, and the warning unit 126 are not shown. FIG. 4(b) is a chart for illustrating frequency characteristics of high-pass filters 160a to 160d in FIG. 4(a).

The occupant information sensing device 100A is different from the occupant information sensing device 100 according to the first embodiment in the following three points. More specifically, as shown in FIG. 4(a), the occupant information sensing device 100A is provided with a second heater power source 162 as a non-insulated type, commonly grounded AC power source to feed power to the two heater electrodes 106 and 108 in place of the first heater power sources 118a and 118b. The occupant information sensing device 100A is provided with the high-pass filters 160a to 160d between the second heater power source 162 and the switching elements 120a to 120d. Furthermore, the occupant information sensing device 100A is not provided with the capacitor 124a described above, and the heartbeat detecting circuit 124 is directly connected with the heater electrodes 106 and 108.

The high-pass filters 160a to 160d have frequency characteristics shown in FIG. 4(b), pass the frequency band of the AC power source of the second heater power source 162 and blocks the frequency band of the heartbeat signals 136 and 138 (for example about 1 Hz to 100 Hz) different from the frequency band of the AC power source.

The occupant information sensing device 100A controls the switching elements 120a to 120d by control signals 130a to 130d and activates or deactivates the heater function by establishing a conduction state or a non-conduction state between the second heater power source 162 and the heater electrodes 106 and 108.

In addition, in the occupant information sensing device 100A, the heartbeat signals 136 and 138 are blocked by the high-pass filters 160a to 160d when the region between the second heater power source 162 and the heater electrodes 106 and 108 is in a conduction state, and the non-insulated type, second heater power source 162 is regarded as having low input impedance. In short, in the occupant information sensing device 100A, the high-pass filters 160a to 160d, the heater electrodes 106 and 108, and the input portion of the heartbeat detecting circuit 124 may be arranged appropriately so that the heater electrodes 106 and 108 appear to have high input impedance to the heartbeat signals 136 and 138. As an example, the input portion of the heartbeat detecting circuit 124 may be connected between the high-pass filters 160b and 160d and the heater electrodes 106 and 108, respectively.

In this way, in the occupant information sensing device 100A, the heartbeat signals 136 and 138 are not passed to the side of the second heater power source 162, and the heartbeat signals 136 and 138 can be received at the heartbeat detecting circuit 124, which activates the heartbeat detecting function.

Therefore, in the occupant information sensing device 100A according to the second embodiment, the non-insulated type, second heater power source 162 and the high-pass filters 160a to 160d are provided, so that the heartbeat detecting function as well as the heater function can be implemented using the heater electrodes 106 and 108. Moreover, the insulated-type, first heater power sources 118a and 118b are not provided, and therefore the manufacturing cost may be reduced.

Furthermore, as described above, when the region between the second heater power source 162 and the heater electrodes 106 and 108 is in a conduction state, the heartbeat detecting function may be activated by the operation of the high-pass filters 160a to 160d. Therefore, if the heater function is kept activated, the heartbeat detecting function by the heartbeat detecting circuit 124 may be implemented using the high-pass filters 160a to 160d that block the heartbeat signals 136 and 138 without providing the switching elements 120a to 120d.

Figure 5:
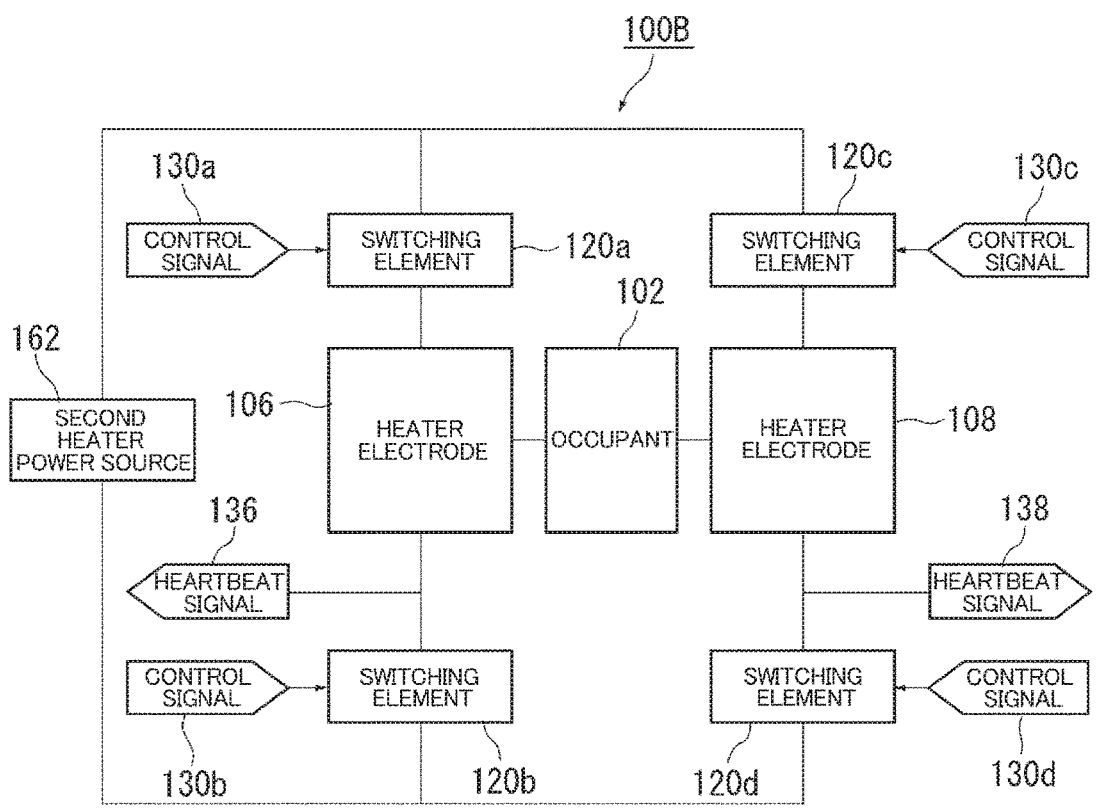
FIG. 5 is an exemplary schematic diagram of an occupant information sensing device according to a third embodiment of the present invention.

FIG. 5 is an exemplary schematic diagram of an occupant information sensing device 100B according to a third embodiment of the present invention. In the figure, the ECU 122, the heartbeat detecting circuit 124, and the warning unit 126 are not shown. The occupant information sensing device 100B is different from the occupant information sensing device 100A according to the second embodiment in that the high-pass filters 160a to 160d are not provided and the heater control circuit 128 in the ECU 122 is used to switch among the switching elements 120a to 120d by time division multiplexing.

In the occupant information sensing device 100B, when the region between the second heater power source 162 and the heater electrodes 106 and 108 is in a conduction state, and the non-insulated type, second heater power source 162 is regarded as having low input impedance, the heartbeat signals 136 and 138 are passed to the side of the second heater power source 162. More specifically, when the switching elements 120a to 120d are turned on, the heater function is activated, while the heartbeat signals 136 and 138 are not received at the heartbeat detecting circuit 124, which deactivates the heartbeat detecting function. On the other hand, when the switching elements 120a to 120d are turned off, the region between the second heater power source 162 and the heater electrodes 106 and 108 attains a non-conduction state, which deactivates the heater function, while the heartbeat signals 136 and 138 are received at the heartbeat detecting circuit 124, which activates the heartbeat detecting function.

Therefore, in the occupant information sensing device 100B, the heater control circuit 128 switches among the switching elements 120a to 120d by time division multiplexing and thus carries out such control that the heater electrodes 106 and 108 are connected to either the second heater power source 162 or the heartbeat detecting circuit 124. However, the time division timing may be set by the physical condition determining unit 148 in the ECU 122 that monitors the heartbeat signal 146 (see FIG. 1).

Figure 6:
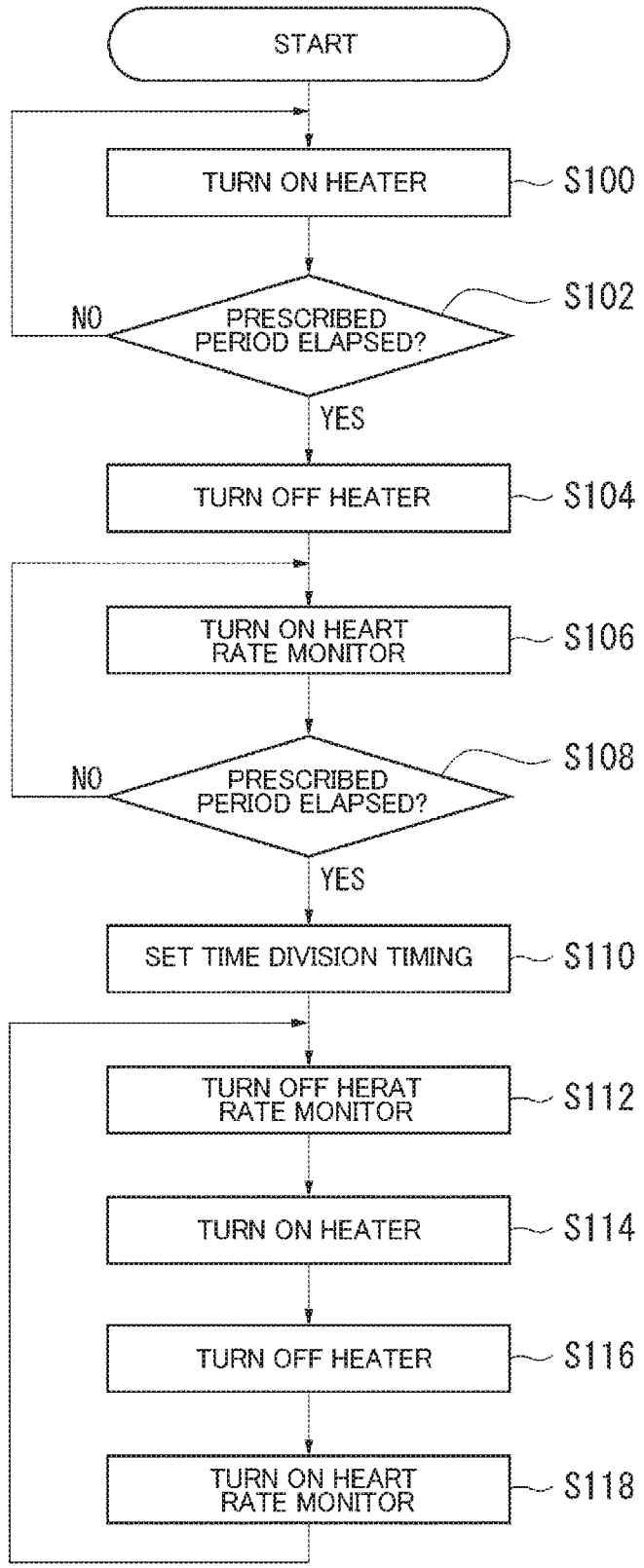
FIG. 6 is an exemplary flowchart for illustrating the operation of the occupant information sensing device in FIG. 5.

FIG. 6 is a flowchart for illustrating the operation of the occupant information sensing device 100B in FIG. 5. To start with, the heater control circuit 128 turns on the switching elements 120a to 120d to conduct the heater electrodes 106 and 108 and activate the heater function (step S100). Then, the heater control circuit 128 determines whether a prescribed time period has elapsed and the temperatures of the heater electrodes 106 and 108 have been raised to a prescribed temperature (step S102) and turns off the switching elements 120a to 120d to deactivate the heater function if the prescribed time period has elapsed (Yes) step S104. If the prescribed time period has not elapsed in step S102 (No), the processing in step S100 is continued.

The physical condition determining unit 148 then receives the heartbeat signal 146 output from the heartbeat detecting circuit 124 and starts to monitor the heart rate (step S106). The physical condition determining unit 148 then determines whether the heart rate has been monitored for a prescribed time period (step S108) and sets the timing for time division control to be carried out by the heater control circuit 128 if the prescribed time period has elapsed (Yes) (step S110). If the prescribed time period has not elapsed in step S108 (No), the processing in step S106 is continued.

Figure 7:
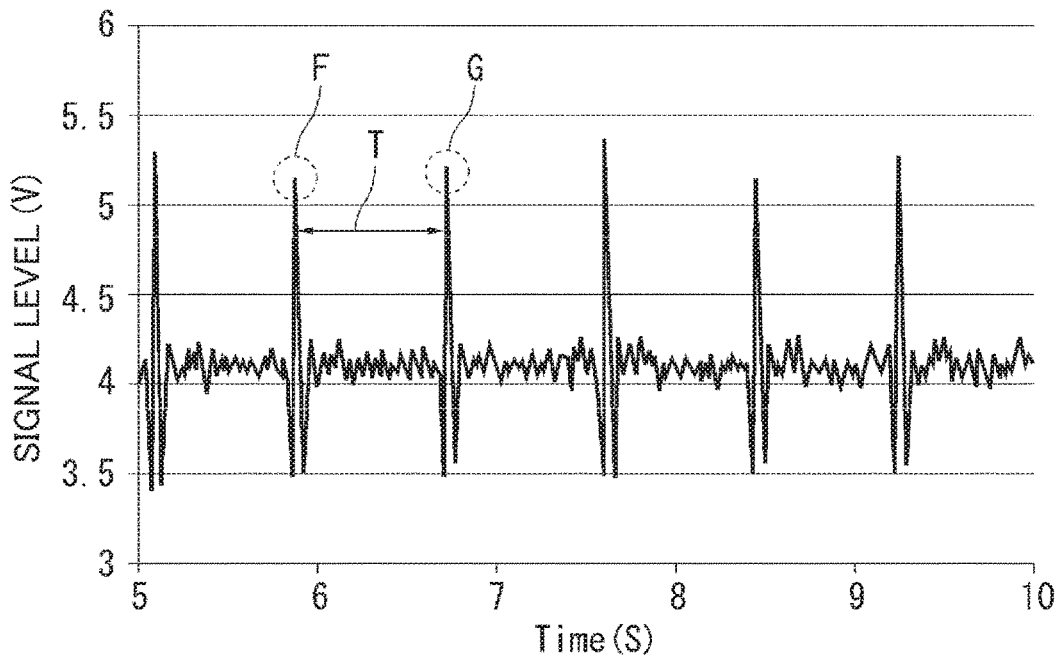
FIGS. 7(a) and 7(b) include exemplary charts showing examples of how to set time division timing in the occupant information sensing device in FIG. 5.
Figure 7:
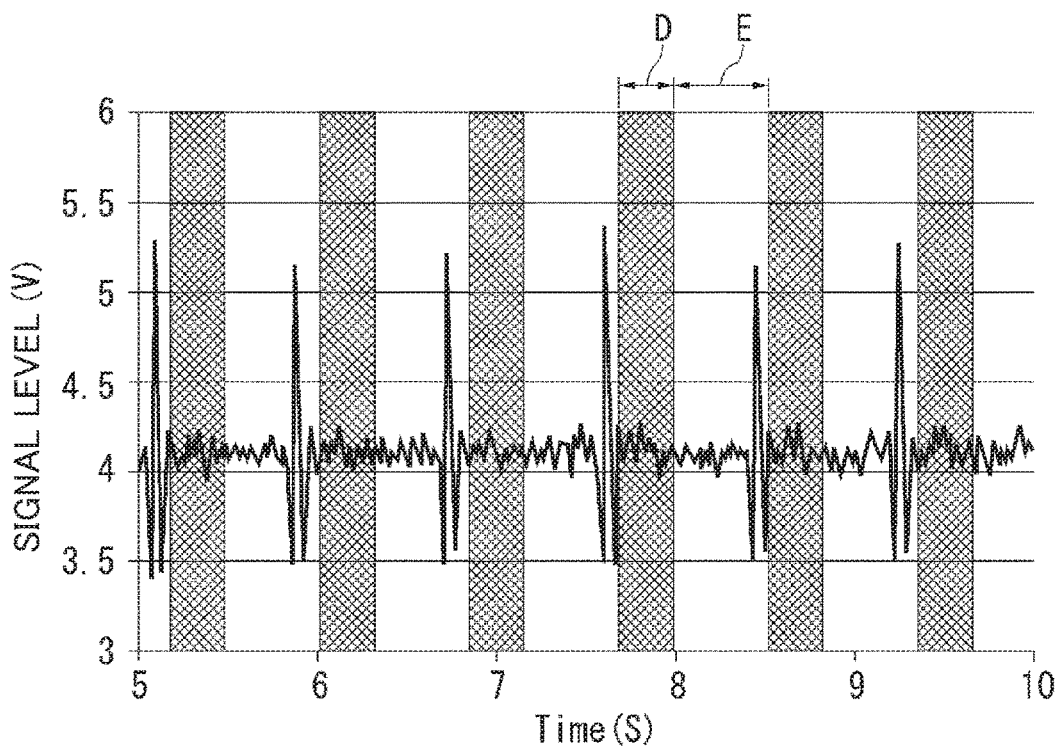

Now, referring to FIG. 7, the processing in steps S108 and S110 will be described. FIG. 7 includes charts for illustrating examples of how to set time division timing in the occupant information sensing device 100B in FIG. 5. FIG. 7(a) is a graph showing a heartbeat waveform. In the graph, the abscissa represents time (s) and the ordinate represents the signal level (V). FIG. 7(b) is a graph showing a heater driving period D and a heartbeat monitoring period E in addition to the heartbeat waveform in FIG. 7(a). The heater driving period D is a period in which the switching elements 120a to 120d are turn on and the heater function is activated. The heartbeat monitoring period E is a period in which the switching elements 120a to 120d are turned off and the heartbeat detecting function is activated.

The physical condition determining unit 148 monitors the heart rate for a specified time period (10 seconds in this example) in the processing in step S108 and obtains the heartbeat waveform shown in FIG. 7(a). The physical condition determining unit 148 then calculates the average heart rate for the specified time period in the processing in step S110 and measures the time T between the peaks F and G in the heartbeat waveform. Further in the processing in the step S110, the physical condition determining unit 148 sets a heater driving period D which is shorter than the time T between the peaks F and G as illustrated in FIG. 7(b). As an example, when the heart rate is 60 BPM, the time T is one second, and the heater driving period D may be set for example to 500 ms. The heartbeat monitoring period E is obtained by removing the heater driving period D from the time T. In this way, the physical condition determining unit 148 sets the timing for time division control by the heater control circuit 128.

Referring back to FIG. 6, the heater control circuit 128 turns on the switching elements 120a to 120d to end monitoring of the heart rate on the basis of the timing for time division control set in step S110 (step S112) and activates the heater function (step S114). The heater control circuit 128 turns off the switching elements 120a to 120d to deactivate the heater function on the basis of the timing for time division control (step S116), starts to monitor the heart rate (step S118) and then carries out the processing in step S112 again.

Therefore, in the occupant information sensing device 100B according to the third embodiment, the non-insulated type, second heater power source 162 is provided, and the switching elements 120a to 120d are switched by time division, so that the heartbeat detecting function can be implemented in addition to the heater function using the heater electrodes 106 and 108.

Figure 8:
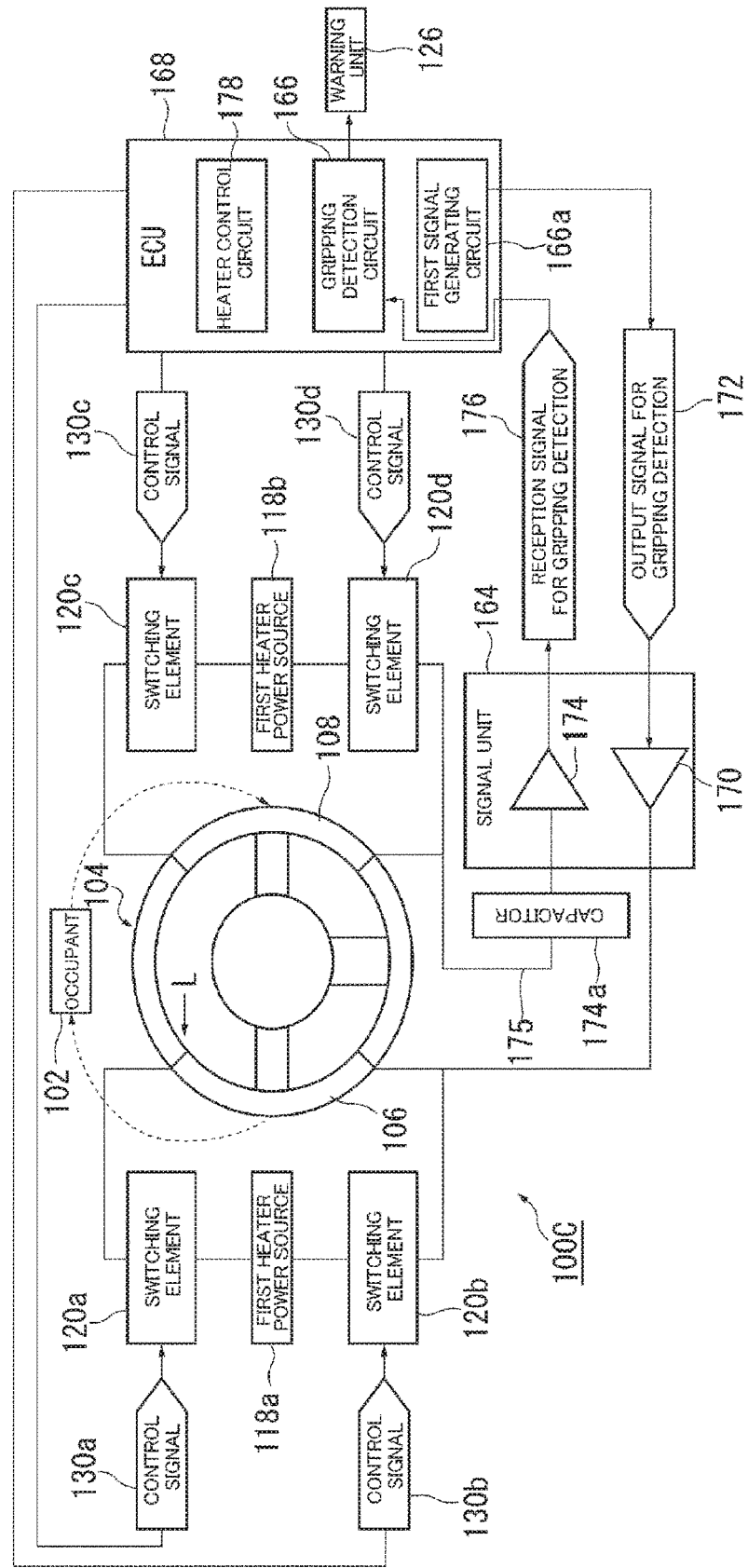
FIG. 8 is an exemplary schematic diagram of an occupant information sensing device according to a fourth embodiment of the present invention.

FIG. 8 is a view for illustrating an occupant information sensing device 100C according to a fourth embodiment of the present invention. The occupant information sensing device 100C is different from the occupant information sensing device 100 according to the first embodiment in the following points. More specifically, the occupant information sensing device 100C detects the gripping state of the steering wheel 104 by the occupant 102 in place of the heartbeat of the occupant 102. Therefore, the occupant information sensing device 100C is provided with a signal unit 164, a signal processing circuit (gripping detecting circuit 166), a first signal generating circuit 166a, and a capacitor 174a in place of the heartbeat detecting circuit 124, the capacitor 124a, and the physical condition determining unit 148.

The first signal generating circuit 166a in an ECU 168 generates a first signal (output signal for gripping detection 172) and inputs the output signal for gripping detection 172 to the heater electrode 106 through an analog circuit 170 as a signal output portion for the signal unit 164. As described above, when the left hand of the occupant 102 is in contact with the heater electrode 106 and the right hand is in contact with the heater electrode 108, the occupant 102 is interposed between the heater electrodes 106 and 108 forming an electrode pair as a dielectric.

When the output signal for gripping detection 172 is input to the heater electrode 106, a gripping state detection signal 175 is output from the heater electrode 108 through the occupant 102 as a dielectric. The gripping state detection signal 175 is a signal indicating gripping information (gripping state) about the steering wheel 104 by the occupant 102, and the gripping state is represented as an AC component.

An analog circuit 174 in the signal unit 164 is connected with the heater electrode 108 through a DC cut capacitor 174a. Therefore, the DC component of the gripping state detection signal 175 output from the heater electrode 108 is cut (i.e. blocked or not conducted) by the capacitor 174a. On the other hand, the AC component of the gripping state detection signal 175 indicating the gripping state is output as a second signal (reception signal for gripping detection 176) through the analog circuit 174 as the signal receiver for the signal unit 164 and is received at the gripping detecting circuit 166. The reception signal for gripping detection 176 is the AC component of the gripping state detection signal 175 and included in the gripping state detection signal 175. The first heater power sources 118a and 118b are apparently earthed (grounded) from the heater electrodes 106 and 108 through the occupant 102.

The gripping detecting circuit 166 detects the gripping state of the steering wheel 104 by the occupant 102 on the basis of the reception signal for gripping detection 176. Hereinafter, the state in which the occupant 102 grips the steering wheel 104 with both hands will be referred to as a first state and the other states as a second state. More specifically, in the second state, the occupant 102 grips the steering wheel 104 with only the left hand or the right hand or does not grip the steering wheel at all.

Figure 9:
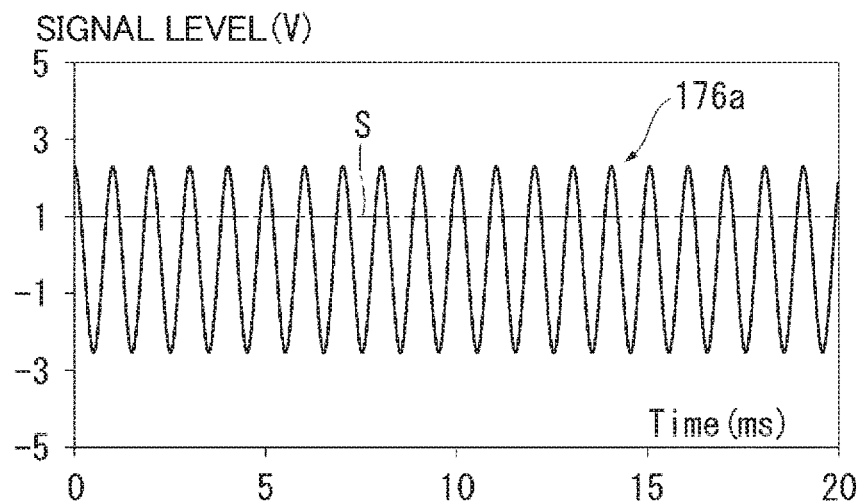
FIGS. 9(a) and 9(b) includes exemplary charts showing waveforms of received electrical signals passed through a pair of electrodes in FIG. 8.
Figure 9:
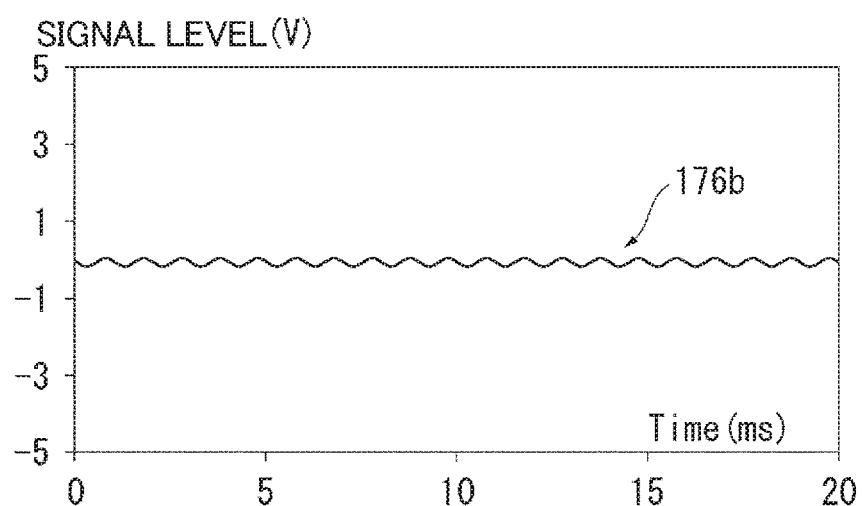

A parameter such as the signal level (voltage value) of the reception signal for gripping detection 176 changes depending on whether the occupant 102 is interposed between the electrode pair, in other words, on whether the first state or the second state is attained. Now, referring to FIG. 9, a variation in the signal level of the reception signal for gripping detection 176 will be described.

FIGS. 9(a) and 9(b) are exemplary waveform charts for an electrical signal received through the electrode pairs in FIG. 8. FIG. 9(a) shows as an example the waveform of a reception signal for gripping detection 176a in the first state. FIG. 9(b) is an exemplary waveform chart for a reception signal for gripping detection 176b in the second state. Note that in the charts, the abscissa represents time (ms), and the ordinate represents the signal level (V). Furthermore, the waveforms of the reception signals for gripping detection 176a and 176b are for example obtained when the signal unit 164 applies the output signal for gripping detection 172 at a frequency of 1 kHz and a voltage of 5 Vpp to the heater electrode 106.

The reception signal for gripping detection 176a in the first state is a signal passed through the occupant 102 as a dielectric and the absolute value of the signal level exceeds 1 V as shown in FIG. 9(a). On the other hand, the reception signal for gripping detection 176b in the second state is a signal obtained when there is no dielectric interposed between the electrode pair. As for the reception signal for gripping detection 176b, the absolute value of the signal level is less than 1 V, and the signal level is lower than the reception signal for gripping detection 176a in the first state as shown in FIG. 9(b).

Therefore, according to the embodiment, the gripping detecting circuit 166 stores, in an appropriate memory, a threshold value S obtained when the signal level indicated by the chain line in FIG. 9(a) is about 1 V and corresponds to the first state. The gripping detecting circuit 166 determines whether the signal level of the reception signal for gripping detection 176 corresponds to the first state or the second state by reading out the threshold value S from the memory.

When the gripping state of the steering wheel 104 is detected as the second state by the gripping detecting circuit 166, the warning unit 126 can output warning using a speaker in the vehicle or the navigation screen of a car navigator to warn the occupant of the abnormality.

A heater control circuit 178 in the ECU 168 controls the switching elements 120a to 120d by the control signals 130a to 130d to establish a conduction state or a non-conduction state between the first heater power sources 118a and 118b and the heater electrodes 106 and 108, which activates or deactivates the heater function.

As described above, in the occupant information sensing device 100C according to the fourth embodiment, the insulated type, first heater power sources 118a and 118b are used, and the heater electrode 108 and the analog circuit 174 of the signal unit 164 are connected through the capacitor 174a. In this way, the gripping detecting circuit 166 can receive the reception signal for gripping detection 176 as the AC component of the gripping state detection signal 175. Therefore, in the occupant information sensing device 100C, the gripping detecting function as well as the heater function can be implemented by the same devices, i.e., the heater electrodes 106 and 108. The two first power sources 118a and 118b are provided to feed power to the heater electrodes 106 and 108, respectively, while alternatively, a single common first heater power source may be provided.

Figure 10:
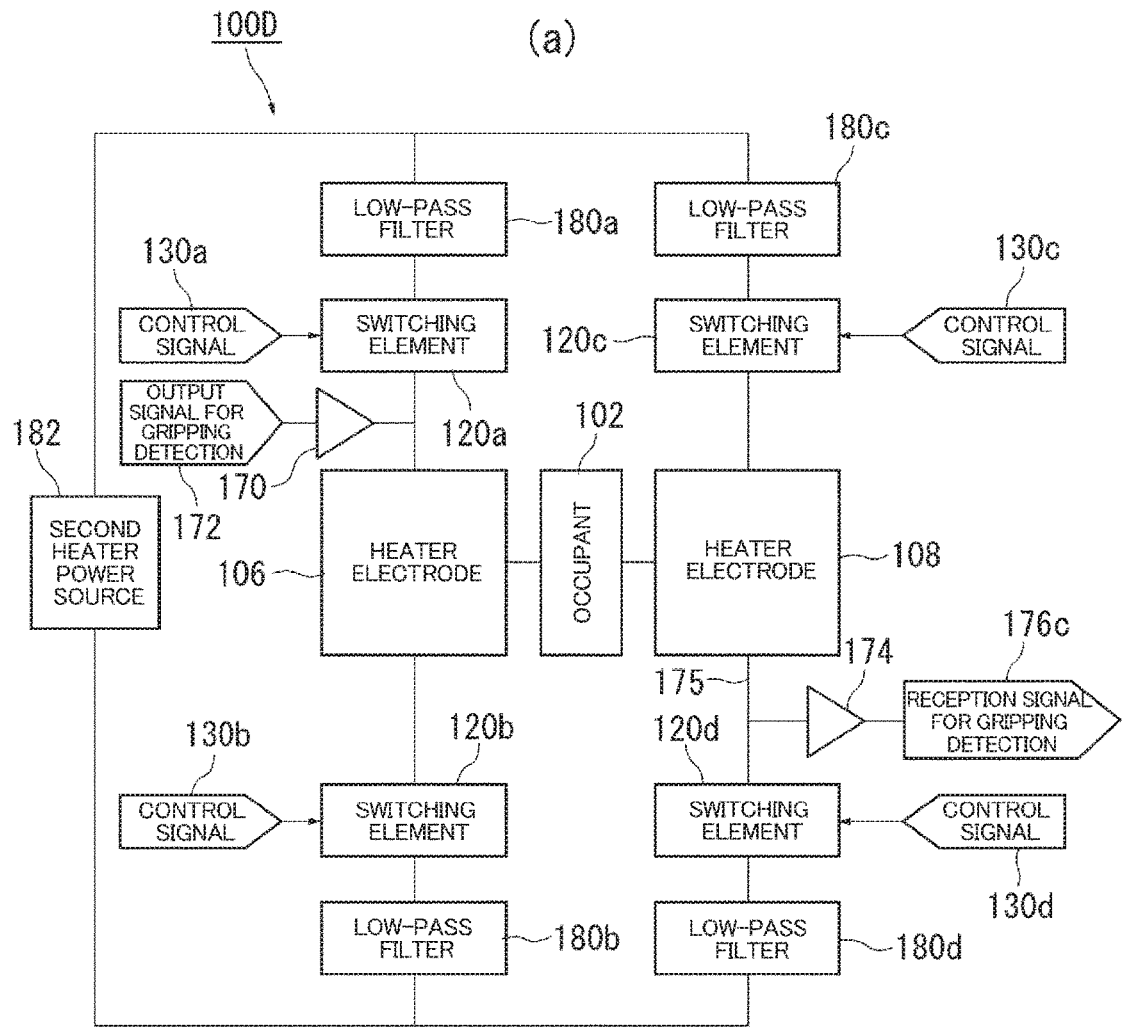
FIGS. 10(a) and 10(b) are exemplary schematic diagrams of an occupant information sensing device according to a fifth embodiment of the present invention.
Figure 10:
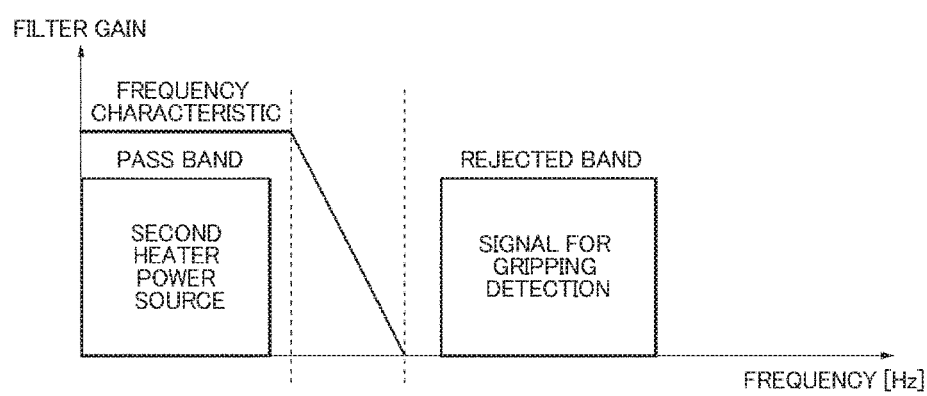

FIG. 10(a) is an exemplary schematic diagram of an occupant information sensing device 100D according to a fifth embodiment of the present invention. FIG. 10(a) is an exemplary functional block diagram showing a part of the occupant information sensing device 100D. In the figure, the signal unit 164, the ECU 168, and the warning unit 126 are not shown. FIG. 10(b) is an exemplary chart for illustrating frequency characteristics of low-pass filters 180a to 180d in FIG. 10(a).

As illustrated in FIG. 10(a), the occupant information sensing device 100D is different from the occupant information sensing device 100C according to the fourth embodiment in the following three points. The occupant information sensing device 100D is provided with a second heater power source 182 as a non-insulated, commonly grounded AC power source that feeds power to the two heater electrodes 106 and 108 in place of the first heater power sources 118a and 118b. The occupant information sensing device 100D is provided with the low-pass filters 180a to 180d between the second heater power source 182 and the switching elements 120a to 120d. Furthermore, the occupant information sensing device 100D is not provided with the above-described capacitor 174a, and the analog circuit 174 of the signal unit 164 and the heater electrode 108 are directly connected.

As illustrated in FIG. 10(a), the output signal for gripping detection 172 is input through the analog circuit 170 connected between the heater electrode 106 and the switching element 120a and upstream of the heater electrode 106. When the output signal for gripping detection 172 is input to the heater electrode 106, the gripping state detection signal 175 is output from the heater electrode 108 through the occupant 102 as a dielectric. The analog circuit 174 is connected between the heater electrode 108 and the switching element 120d and downstream of the heater electrode 108. The gripping state detection signal 175 is output through the analog circuit 174 as a reception signal for gripping detection 176c.

The low-pass filters 180a to 180d have frequency characteristics as shown in FIG. 10(b) and pass the frequency band of the second heater power source 182 as the AC power source and block frequency bands of the output signal for gripping detection 172 and the gripping state detection signal 175 different from the frequency band of the AC power source. In this case, the output signal for gripping detection 172 having too high a frequency is bypassed by a capacitor component formed between the heater electrode 106 of the steering wheel 104 shown in FIG. 8 and the core 110 (see FIG. 1(b)). In this case, if the gripping state of the steering wheel 104 is in the second state, the signal level of the reception signal for gripping detection 176c may become high, and erroneous detection may result. Therefore, the upper limit for the output signal for gripping detection 172 is set to for example about 100 kHz.

In the occupant information sensing device 100D, the switching elements 120a to 120d are controlled in response to the control signals 130a to 130d to establish a conduction state or a non-conduction state between the second heater power source 182 and the heater electrodes 106 and 108, so that the heater function can be activated or deactivated.

When the region between the second heater power source 182 and the heater electrodes 106 and 108 is in a conduction state and the non-insulated, second heater power source 182 is regarded as having low input impedance, the output signal for gripping detection 172 and the gripping state detection signal 175 are blocked by the low-pass filters 180a to 180d. Therefore, the output signal for gripping detection 172 and the gripping state detection signal 175 are not passed to the side of the second heater power source 182, and the reception signal for gripping detection 176c can be received at the gripping detecting circuit 166. In short, in the occupant information sensing device 100D, the low-pass filters 180a to 180d, the heater electrodes 106 and 108, and the signal unit 164 may be appropriately set so that the heater electrodes 106 and 108 appear to have high input impedance to the output signal for gripping detection 172 and the gripping state detection signal 175. As an example, the analog circuits 170 and 174 of the signal unit 164 may be connected between the low-pass filters 180a and 180d and the heater electrodes 106 and 108, respectively.

Therefore, in the occupant information sensing device 100D according to the fifth embodiment, the non-insulated, second heater power source 182 and the low-pass filters 180a to 180d are provided, so that the gripping detecting function as well as the heater function can be implemented using the heater electrodes 106 and 108. Since the insulated type, first heater power sources 118a and 118b are not provided, the manufacturing cost can be reduced.

As described above, when the region between the second heater power source 182 and the heater electrodes 106 and 108 is in a conduction state, the gripping detecting function can be activated by the functions of the low-pass filters 180a to 180d. Therefore, if the heater function is kept active, the gripping detecting function by the gripping detecting circuit 166 may be implemented by the low-pass filters 180a to 180d that block the output signal for gripping detection 172 and the gripping state detection signal 175 without providing the switching elements 120a to 120d.

Figure 11:
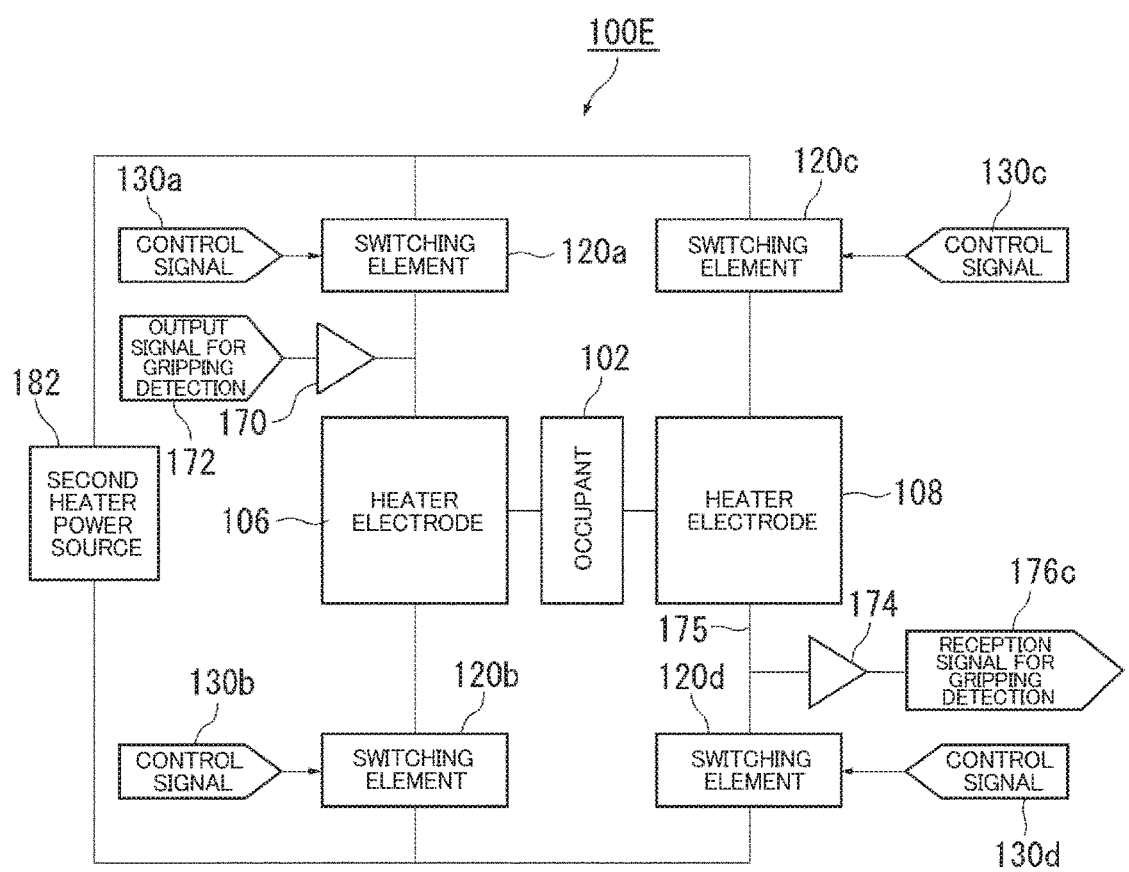
FIG. 11 is an exemplary schematic diagram of an occupant information sensing device according to a sixth embodiment of the present invention.

FIG. 11 is an exemplary schematic diagram of an occupant information sensing device 100E according to a sixth embodiment of the present invention. In the figure, the ECU 168, the signal unit 164, and the warning unit 126 are not shown. The occupant information sensing device 100E is different from the occupant information sensing device 100D according to the fifth embodiment in that the low-pass filters 180a to 180d are not provided and the switching elements 120a to 120d are switched by time division by the heater control circuit 178 in the ECU 168.

In the occupant information sensing device 100E, when the region between the second heater power source 182 and the heater electrodes 106 and 108 is in a conduction state and the non-insulated type, second heater power source 182 is regarded as having low input impedance, the output signal for gripping detection 172 and the gripping state detection signal 175 are passed to the side of the second heater power source 182. More specifically, when the switching elements 120a to 120d are turned on, the heater function is activated, while the reception signal for gripping detection 176c is not received at the gripping detecting circuit 166 and the gripping detecting function is deactivated. On the other hand, when the switching elements 120a to 120d are turned off, the region between the second heater power source 182 and the heater electrodes 106 and 108 is in a non-conduction state and the heater function is deactivated, while the reception signal for gripping detection 176c is received at the gripping detecting circuit 166 and the gripping detecting function is activated.

Therefore, in the occupant information sensing device 100E, the heater control circuit 178 carries out control to connect the heater electrodes 106 and 108 to one of the second heater power source 182 and the gripping detecting circuit 166 by switching among the switching elements 120a to 120d by time division.

Figure 12:
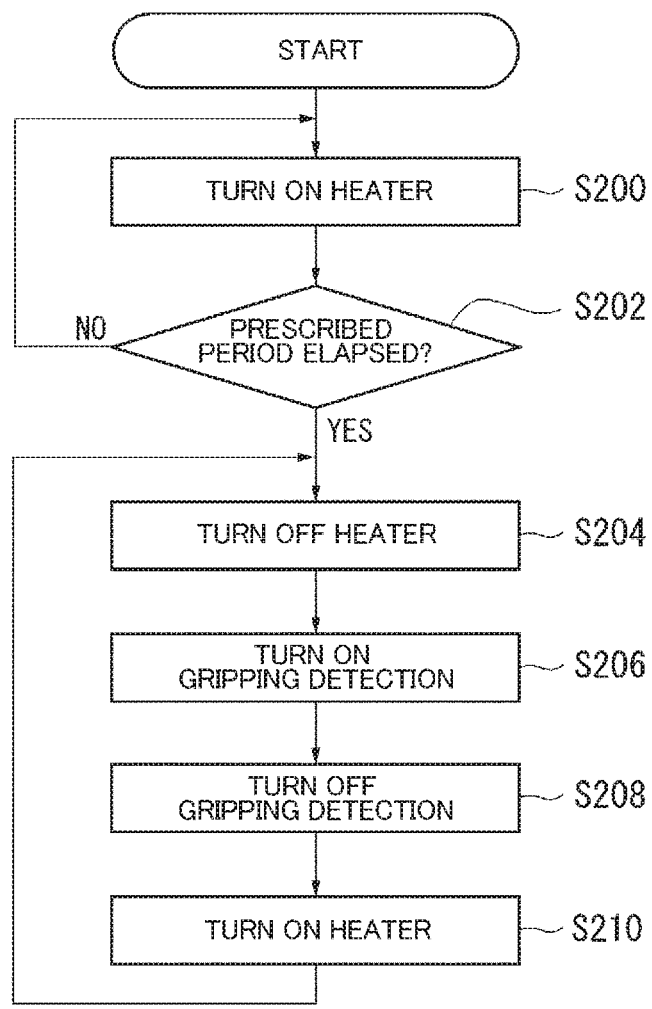
FIG. 12 is an exemplary flowchart for illustrating the operation of the occupant information sensing device in FIG. 11.

FIG. 12 is an exemplary flowchart for illustrating the operation of the occupant information sensing device 100E in FIG. 11. The heater control circuit 178 turns on the switching elements 120a to 120d to establish a conduction state between the heater electrodes 106 and 108, thus activating the heater function (step S200). Then, the heater control circuit 178 determines whether a prescribed time period has elapsed and the temperatures of the heater electrodes 106 and 108 have been raised to a prescribed temperature (step S202) and turns off the switching elements 120a to 120d if the prescribed time period has elapsed (Yes), thus deactivating the heater function (step S204). If the prescribed time period has not elapsed in step S202 (No), the processing in step S200 is continued.

Then, the gripping detecting circuit 166 inputs the output signal for gripping detection 172 to the heater electrode 106, receives the reception signal for gripping detection 176c output through the analog circuit 174 from the heater electrode 108 and detects the gripping state (step S206). Then, for example after a prescribed time period, the gripping detecting circuit 166 ends detection of the gripping state for example by stopping inputting the reception signal for gripping detection 172 to the heater electrode 106 (step S208). However, in step S208, the heater control circuit 178 may turn on the switching elements 120a to 120d, so that the reception signal for gripping detection 176c is not received at the gripping detecting circuit 166, and detection of the gripping state may end as a result.

Then, the heater control circuit 178 turns on the switching elements 120a to 120d to activate the heater function (step S210) and again carries out the processing in step S204 for example after a prescribed time period.

Therefore, in the occupant information sensing device 100E according to the sixth embodiment, the non-insulated type, second heater power source 182 is provided, and the switching elements 120a to 120d are switched by time division, so that the gripping detecting function as well as the heater function can be implemented using the heater electrodes 106 and 108.

Figure 13:
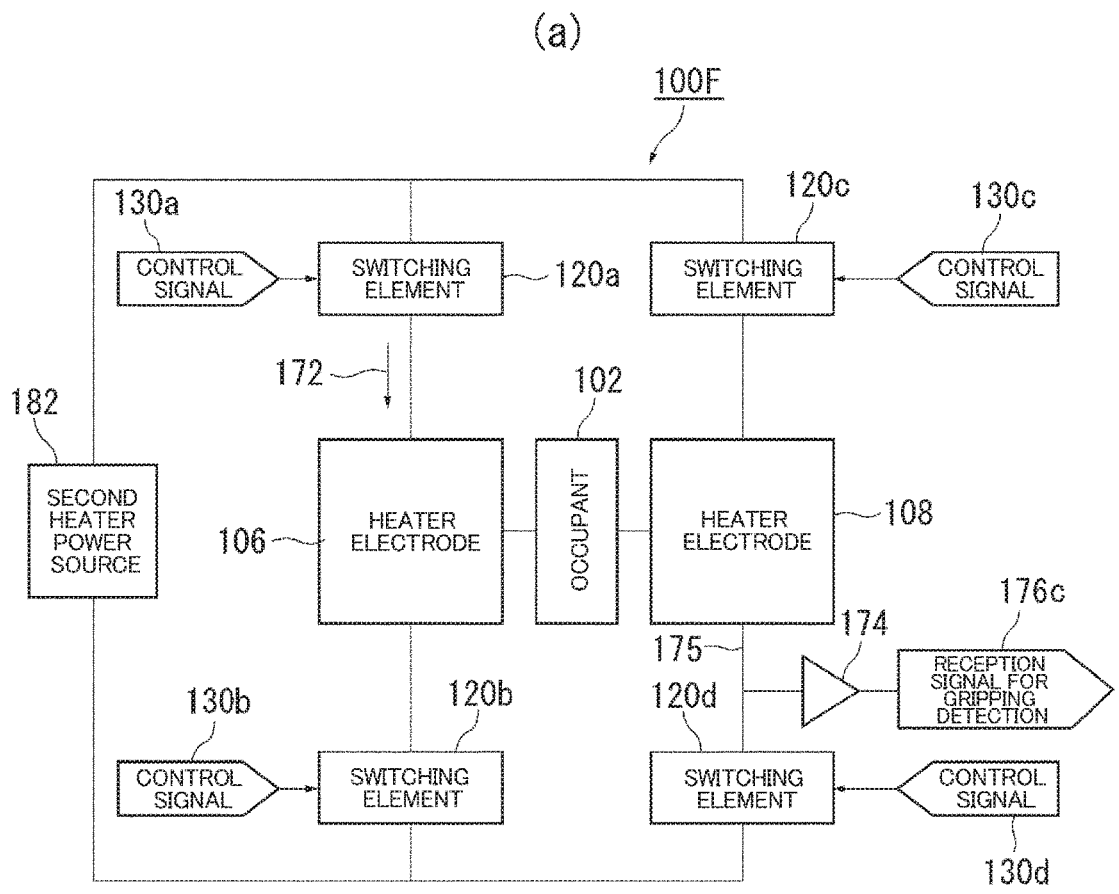
FIGS. 13(a) and 13(b) are exemplary schematic diagrams of an occupant information sensing device according to a seventh embodiment of the present invention.

FIG. 13(a) is an exemplary schematic diagram of an occupant information sensing device 100F according to a seventh embodiment of the present invention. FIG. 13(a) is an exemplary functional block diagram showing a part of the occupant information sensing device 100F. In the figure, the ECU 168, the signal unit 164, and the warning unit 126 are not shown. FIG. 13(b) shows states of the switching elements 120a to 120d and the like in association with the operation of the occupant information sensing device 100F in FIG. 13(a).

As shown in FIG. 13(a), the occupant information sensing device 100F is different from the occupant information sensing device 100E according to the sixth embodiment in the following points. More specifically, in the occupant information sensing device 100F, the first signal generating circuit 166a in the ECU 168 does not output the output signal for gripping detection 172, and the heater control circuit 178 generates the output signal for gripping detection 172 instead by changing the control signal 130a for the switching element 120a. Therefore, as illustrated in FIG. 13(a), the occupant information sensing device 100F does not need the first signal generating circuit 166a and the analog circuit 170 (see FIG. 8) as a signal output portion for the signal unit 164.

In the occupant information sensing device 100F, the heater control circuit 178 generates the output signal for gripping detection 172 for example by changing gate voltage, i.e., the control signal 130a applied to the switching element 120a. As an example, if a necessary output signal for gripping detection 172 is a sine wave at 10 kHz, the control signal 130a may be changed into the same sine wave at 10 kHz and applied to the switching element 120a. In this way, the switching element 120a has drain current varied in response to a variation in the applied gate voltage, and the output signal for gripping detection 172 is generated. Note that the heater control circuit 178 may generate the output signal for gripping detection 172 by changing the control signal 130b applied to the switching element 120b.

In the occupant information sensing device 100F, when the region between the second heater power source 182 and the heater electrodes 106 and 108 is in a conduction state, the non-insulated type, second heater power source 182 is regarded as having low input impedance. Then, the heater control circuit 178 switches among the switching elements 120a to 120d by time division to connect the heater electrodes 106 and 108 to one of the second heater power source 182 and the gripping detecting circuit 166 and further generates the output signal for gripping detection 172 using the switching element 120a.

More specifically, in the occupant information sensing device 100F, as illustrated in FIG. 13(b), the heater function can be activated by turning on the switching elements 120a to 120d and deactivated by turning off the switching elements. In this case, when the switching elements 120a to 120d are off, the output signal for gripping detection 172 is not generated, and therefore the gripping detecting circuit 166 cannot receive the reception signal for gripping detection 176c, so that the gripping detecting function is deactivated.

Therefore, in the occupant information sensing device 100F, the control signal 130a is changed by tuning on only the switching element 120a to generate the output signal for gripping detection 172, and the gripping detecting circuit 166 surely receives the reception signal for gripping detection 176c. At the time, if the gripping state of the steering wheel 104 by the occupant 102 is in the first state, the absolute value of the signal level of the reception signal for gripping detection 176a exceeds 1 V as illustrated in FIG. 9(a). On the other hand, if the gripping state is in the second state, the absolute value of the signal level of the reception signal for gripping detection 176b is less than 1 V which is lower than the signal level in the first state as illustrated in FIG. 9(b). In this way, in the occupant information sensing device 100F, the gripping detecting function by the gripping detecting circuit 166 can be activated or deactivated.

Therefore, in the occupant information sensing device 100F according to the seventh embodiment, the non-insulated type, second heater power source 182 is provided, the control signal 130a for the switching element 120a for example is changed while the switching elements 120a to 120d are switched by time division, so that the gripping detecting function as well as the heater function can be implemented using the heater electrodes 106 and 108.

FIGS. 14(a) and (b) are exemplary schematic diagrams of an occupant information sensing device 100G according to an eighth embodiment of the present invention. FIG. 14(a) is an exemplary functional block diagram showing a part of the occupant information sensing device 100G. In the figure, the ECU 168, the signal unit 164, and the warning unit 126 are not shown. FIG. 14(b) shows states of the switching elements 120a to 120d and the like in association with the operation of the occupant information sensing device 100G in FIG. 14(a).

The occupant information sensing device 100G is different from the occupant information sensing device 100E according to the sixth embodiment in that the heater control circuit 178 controls the switching elements 120a to 120d by time division and the switching elements 120a and 120d are switched in order to electrically stimulate the occupant 102.

In the occupant information sensing device 100G, when the region between the second heater power source 182 and the heater electrodes 106 and 108 is in a conduction state, the non-insulated type, second heater power source 182 is regarded as having low input impedance similarly to the above. Therefore, the heater control circuit 178 switches the switching elements 120a to 120d by time division to connect the heater electrodes 106 and 108 to one of the second heater power source 182 and the gripping detecting circuit 166.

More specifically, in the occupant information sensing device 100G, as illustrated in FIG. 14(b), the heater function may be activated or deactivated by turning on or off the switching elements 120a to 120d. When the switching elements 120a to 120d are off, the output signal for gripping detection 172 is input to the heater electrode 106. The reception signal for gripping detection 176c output through the analog circuit 174 from the heater electrode 108 is received at the gripping detecting circuit 166, so that the gripping detecting function is activated.

Furthermore, in the occupant information sensing device 100G, as illustrated in FIG. 14(b), the switching elements 120a and 120d are turned on in order to electrically stimulate the occupant 102. In this way, an electrical signal 184 output from the second heater power source 182 is passed through the switching element 120a and the occupant 102 as a dielectric from the heater electrode 106 and further to the side of the second heater power source 182 from the heater electrode 108 through the switching element 120d.

The electrical signal 184 output from the second heater power source 106 has a higher signal level than the output signal for gripping detection 172 and the gripping state detection signal 175 and can therefore electrically stimulate the skin surface of the occupant 102. As illustrated in FIG. 13(b), in the occupant information sensing device 100G, the switching element 120d is switched between on and off states in prescribed timing while the switching element 120a is kept on, so that patterns of the electric stimulation given to the occupant 102 can be appropriately adjusted. Note that the analog circuit 174 as the signal receiving portion for the signal unit 164 has for example several kΩ input impedance, and the electrical signal 184 is not received at the gripping detecting circuit 166 and is not erroneously detected.

Figure 14:
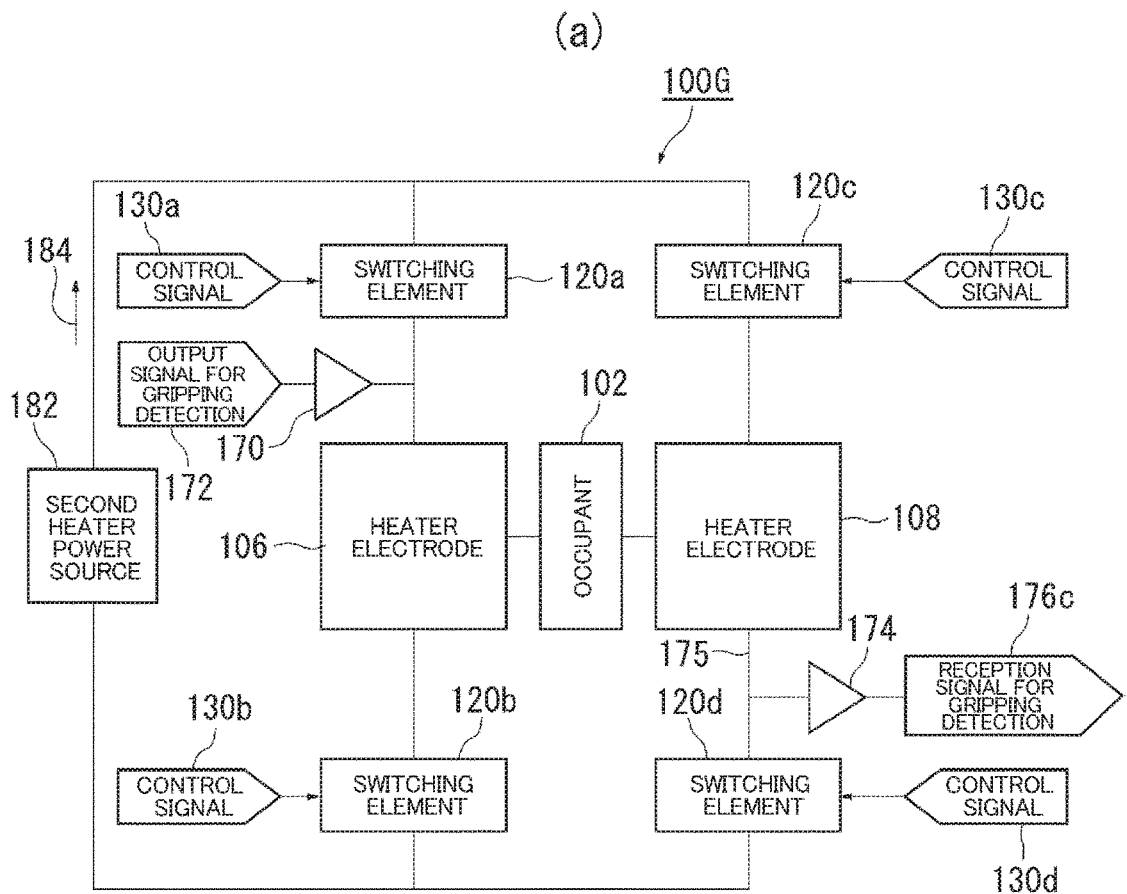
FIGS. 14(a) and 14(b) are exemplary schematic diagrams of an occupant information sensing device according to an eighth embodiment of the present invention.
Figure 15:
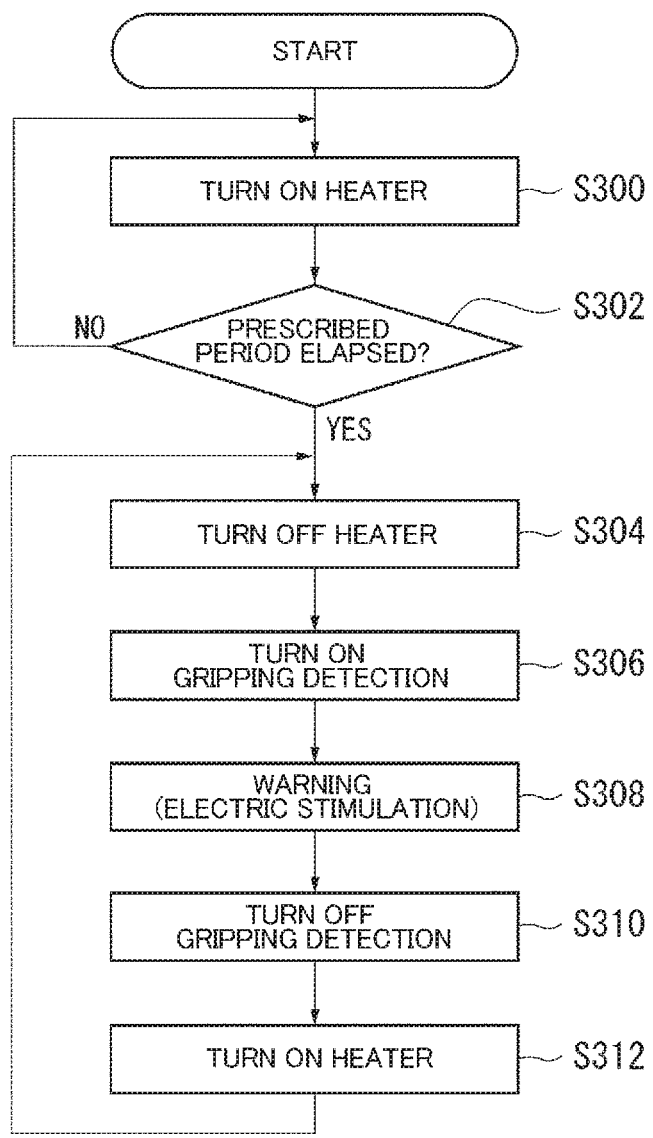
FIG. 15 is a flowchart for illustrating the operation of the occupant information sensing device in FIG. 14.

FIG. 15 is a flowchart for illustrating the operation of the occupant information sensing device 100G in FIG. 14. To start with, the heater control circuit 178 turns on the switching elements 120a to 120d to conduct the heater electrodes 106 and 108 and activate the heater function (step S300). Then, the heater control circuit 178 determines whether a prescribed time period has elapsed and the temperatures of the heater electrodes 106 and 108 have been raised to a prescribed temperature (step S302) and turns off the switching elements 120a to 120d to deactivate the heater function if the prescribed time period has elapsed (Yes) (step S304). If the prescribed time period has not elapsed in step S302 (No), the processing in step S300 is continued.

The gripping detecting circuit 166 inputs the output signal for gripping detection 172 to the heater electrode 106, receives the reception signal for gripping detection 176c output from the heater electrode 108 through the analog circuit 174 and detects the gripping state (step S306). Then, for example after a prescribed time period, the heater control circuit 178 turns on switching elements 120a and 120d and electrically stimulates the occupant 102 (step S308). The electric stimulation in step S308 serves as warning different from audio or visual warning.

The gripping detecting circuit 166 ends the detection of the gripping state by stopping inputting the output signal for gripping detection 172 to the heater electrode 106 (step S310). Note however that in step S310, the heater control circuit 178 may turn on the switching elements 120a to 120d, so that the reception signal for gripping detection 176 is not received at the gripping detecting circuit 166 and the detection of the gripping state may end as a result.

Then, the heater control circuit 178 turns on the switching elements 120a to 120d to activate the heater function (step S312) and again carries out the processing in step S304 for example after a prescribed time period.

In this way, in the occupant information sensing device 100G, the non-insulated type, second heater power source 182 is provided, and for example the switching elements 120a and 120d are switched between on and off states while the switching elements 120a to 120d are switched by time division. Therefore, using the heater electrodes 106 and 108, warning by electric stimulation can be carried out in addition to the gripping detecting function and the heater function.

In the above-described embodiments, the steering wheel 104 is provided with the two heater electrodes 106 and 108, while alternatively three or more electrodes may be provided if an electrode pair is arranged when the occupant 102 grips the steering wheel 104 by both hands. In this way, when two or more arbitrary heater electrodes are provided at the steering wheel 104, a heater electrode that is not fed from the first and second heater electrodes is still capable of outputting a heartbeat signal or a gripping state detection signal. Therefore, the heater electrodes connected to the signal processing circuit may include such an unfed electrode. Even in this case, using the heater electrodes, the heartbeat detecting function by the heartbeat detecting circuit 124 and the gripping detecting function by the gripping detecting circuit 166 can be implemented in addition to the heater function.

Among the above-described embodiments, in the occupant information sensing devices 1008, 100E, 100F, and 100G, the heartbeat detecting function or the gripping detecting function is implemented in addition to the heater function using the heater electrodes 106 and 108 by time division control of the switching elements 120a to 120d.

However, the time division control of the switching elements 120a to 120d may be applied to the occupant information sensing devices 100A, 100C, and 100D according to the other embodiments. In this way, the heartbeat detecting function or the gripping detecting function and the heater function can be switched, so that the heartbeat detecting function or the gripping detecting function can surely be implemented in addition to the heater function using the heater electrodes 106 and 108.

Further in the above-described embodiments, only one of the heartbeat detecting circuit 124 and the gripping detecting circuit 166 is employed as the signal processing circuit, but alternatively both the heartbeat detecting circuit 124 and the gripping detecting circuit 166 may be provided. As an example, when the first heater power sources 118a and 118b are used, the gripping detecting circuit 166 and the first signal generating circuit 166a in the occupant information sensing device 100C illustrated in FIG. 8 may be provided in the occupant information sensing device 100 illustrated in FIG. 1(a), and the signal unit 164 and the capacitor 174a may also be provided so that the reception signal for gripping detection 176 can be received without interference with the heartbeat signals 136 and 138.

As an example, when the second heater power source 162 is used, the gripping detecting circuit 166 and the first signal generating circuit 166a are provided in the occupant information sensing device 100A illustrated in FIG. 4(a). Then, the signal unit 164 is provided in the occupant information sensing device 100A so that the reception signal for gripping detection 176c illustrated in FIG. 10(a) can be received without interference with the heartbeat signals 136 and 138. Then, the occupant information sensing device 100A is provided with a band-pass filter that blocks the frequencies of the heartbeat signals 136 and 138 and the frequencies of the output signal for gripping detection 172 and the gripping state detection signal 175 in place of the high-pass filters 160a to 160d. In this way, the heartbeat signals 136 and 138, the output signal for gripping detection 172, and the gripping state detection signal 175 are blocked by the band-pass filter and not passed to the second heater power source 162. Therefore, the heartbeat signals 136 and 138 and the reception signal for gripping detection 176c can be received at the heartbeat detecting circuit 124 and the gripping detecting circuit 166, respectively.

Therefore, both the heartbeat detecting circuit 124 and the gripping detecting circuit 166 are provided as described above, so that the gripping detecting function as well as the heater function can be implemented using the heater electrodes 106 and 108. [0

While the above description constitutes the preferred embodiment of the present invention, it will be appreciated that the invention is susceptible to modification, variation and change without departing from the proper scope and fair meaning of the accompanying claims.

The invention claimed is:

1. An occupant information sensing device, comprising:
    at least two heater electrodes that are provided at a vehicle steering wheel and electrically separated from one another and that generate heat by conduction;
    at least one heater power source in the form of an insulated type DC power source that feeds power to the at least two heater electrodes through a power signal; and
    a signal processor connected to the at least one heater power source and the at least two heater electrodes through a capacitor, and the signal processor configured to process an occupant information signal output from the at least two heater electrodes, wherein the at least two heater electrodes are electrically floating and isolated from an electronic ground by a transformer in the at least one heater power source, and wherein the capacitor is connected directly between the at least two heater electrodes and the signal processor to cut DC components while passing an AC component from the heater electrodes to the signal processor.

2. The occupant information sensing device according to claim 1, the capacitor being connected to an input portion of the signal processor.

3. The occupant information sensing device according to claim 1, further comprising a switch that is provided in a circuit from the at least one heater power source to the at least two heater electrodes and that establishes a conduction state or a non-conduction state between the at least one heater power source and the at least two heater electrodes.

4. The occupant information sensing device according to claim 3, further comprising an electronic control unit (ECU) configured to control the switch by time division multiplexing, wherein the ECU connects the at least two heater electrodes to one of the heater power source and the signal processor at prescribed time intervals.

5. The occupant information sensing device according to claim 1 further comprising wherein the signal processor includes a heartbeat detector configured to detect a heartbeat of an occupant by differentially amplifying heartbeat signals from the occupant output from the at least two heater electrodes.

6. The occupant information sensing device according to claim 1 further comprising, wherein the signal circuit processor further includes a first signal generator configured to supply a first signal to one of the at least two heater electrodes and a gripping detector configured to detect a state of gripping the steering wheel by the occupant on the basis of a second signal, the first signal that has passed through the occupant in contact with one and the other of the at least two heater electrodes being output from the other as the second signal.

7. The occupant information sensing device according to claim 1 further comprising switches operable to electrically stimulate the occupant.

8. An occupant information sensing device for a steering wheel, comprising:
at least two heater electrodes that are provided at the vehicle steering wheel and electrically separated from one another and that generate heat by conduction;
at least one heater power source in the form of an insulated type DC power source that feeds power to the at least two heater electrodes through a power signal; and
a signal processor connected to the at least two heater electrodes and configured to process an occupant information signal output from the at least two heater electrodes, wherein the at least two heater electrodes are electrically floating and isolated from an electronic ground by a transformer in the at least one heater power source, and wherein a capacitor connected directly between the at least two heater electrodes and the signal processor to cut DC components while passing an AC component from the heater electrodes to the signal processor.

9. An occupant information sensing device, comprising:
at least two heater electrodes that are provided at a vehicle steering wheel and electrically separated from one another and that generate heat by conduction;
at least one heater power source in the form of an insulated type DC power source that feeds power through a power signal to a first electrode of the at least two heater electrodes though a transformer insulating the heater electrodes from electrical ground;
a signal processor connected to the at least one heater power source and the first electrode of the at least two heater electrodes through a capacitor, the signal processor processing an occupant information signal output from the at least two heater electrodes, wherein the at least two heater electrodes are electrically floating and isolated from an electronic ground by the transformer in the at least one heater power source, and wherein the capacitor is connected directly between the at least two heater electrodes and the signal processor to cut DC components while passing an AC component from the heater electrodes to the signal processor;
a switch configured in a first mode to connect the power source between the first electrode of the at least two heater electrodes and the capacitor; and
an electronic control unit (ECU) configured to control the switch by time division multiplexing, wherein the ECU connects the at least two heater electrodes to one of the heater power source and the signal processor at prescribed time intervals.

* * * * *